(12) United States Patent
Tung et al.

(10) Patent No.: US 9,260,432 B2
(45) Date of Patent: Feb. 16, 2016

(54) SUBSTITUTED DERIVATIVES OF BICYCLIC [4.3.0] HETEROARYL COMPOUNDS

(75) Inventors: Roger D. Tung, Lexington, MA (US); Craig E. Masse, Cambridge, MA (US)

(73) Assignee: Concert Pharmaceuticals, Inc., Lexington, MA (US)

(*) Notice: Subject to any disclaimer, the term of this patent is extended or adjusted under 35 U.S.C. 154(b) by 643 days.

(21) Appl. No.: 13/394,025

(22) PCT Filed: Sep. 1, 2010

(86) PCT No.: PCT/US2010/047557
§ 371 (c)(1),
(2), (4) Date: Aug. 14, 2012

(87) PCT Pub. No.: WO2011/028820
PCT Pub. Date: Mar. 10, 2011

(65) Prior Publication Data
US 2012/0295925 A1    Nov. 22, 2012

Related U.S. Application Data

(60) Provisional application No. 61/239,371, filed on Sep. 2, 2009.

(51) Int. Cl.
| C07D 487/04 | (2006.01) |
| A61K 31/519 | (2006.01) |
| A61P 13/12 | (2006.01) |
| A61P 7/00 | (2006.01) |
| C07D 513/04 | (2006.01) |
| A61P 1/16 | (2006.01) |

(52) U.S. Cl.
CPC ............ *C07D 487/04* (2013.01); *C07D 513/04* (2013.01); *C07B 2200/05* (2013.01)

(58) Field of Classification Search
CPC ........................... C07D 487/04; A61K 31/519
USPC ........................................ 544/280; 514/265.1
See application file for complete search history.

(56) References Cited

U.S. PATENT DOCUMENTS

| 5,112,827 A | 5/1992 | Saunders et al. |
| 5,648,357 A | 7/1997 | Bianco et al. |
| 5,780,476 A | 7/1998 | Underiner et al. |
| 6,020,337 A | 2/2000 | Leigh et al. |
| 6,221,335 B1 | 4/2001 | Foster |
| 6,316,458 B1 | 11/2001 | Nadler et al. |
| 6,420,374 B1 | 7/2002 | Bianco et al. |
| 6,440,710 B1 | 8/2002 | Keinan et al. |
| 6,603,008 B1 | 8/2003 | Ando et al. |
| 6,774,130 B2 * | 8/2004 | Klein et al. ............... 514/263.2 |
| 6,878,715 B1 | 4/2005 | Klein et al. |
| 7,517,990 B2 | 4/2009 | Ito et al. |
| 8,263,601 B2 | 9/2012 | Tung et al. |
| 2005/0107420 A1 | 5/2005 | Armstrong et al. |
| 2007/0082929 A1 | 4/2007 | Gant et al. |
| 2007/0197695 A1 | 8/2007 | Potyen et al. |
| 2008/0103122 A1 | 5/2008 | Veltri |
| 2008/0249089 A1 | 10/2008 | Himmelsbach et al. |
| 2009/0149399 A1 | 6/2009 | Tung |
| 2009/0239886 A1 | 9/2009 | Tung et al. |
| 2011/0053961 A1 | 3/2011 | Tung et al. |
| 2011/0059995 A1 | 3/2011 | Tung et al. |
| 2011/0077255 A1 | 3/2011 | Tung et al. |
| 2012/0202830 A1 | 8/2012 | Tung et al. |
| 2014/0121226 A1 | 5/2014 | Tung et al. |

FOREIGN PATENT DOCUMENTS

| WO | 87/00523 A2 | 1/1987 |
| WO | 94/22449 A1 | 10/1994 |

(Continued)

OTHER PUBLICATIONS

Nicklasson et al., "Stereoselective Metabolism of Pentoxifylline In Vitro and In Vivo in Humans," Chirality 14:643-652 (2002).

(Continued)

*Primary Examiner* — Susanna Moore
(74) *Attorney, Agent, or Firm* — McCarter & English, LLP; Steven G. Davis; Emily Dertz

(57) ABSTRACT

This invention relates to novel compounds of the Formula A, B, or C, and pharmaceutically acceptable salts thereof. This invention also provides compositions comprising one or more compounds of this invention and a carrier.

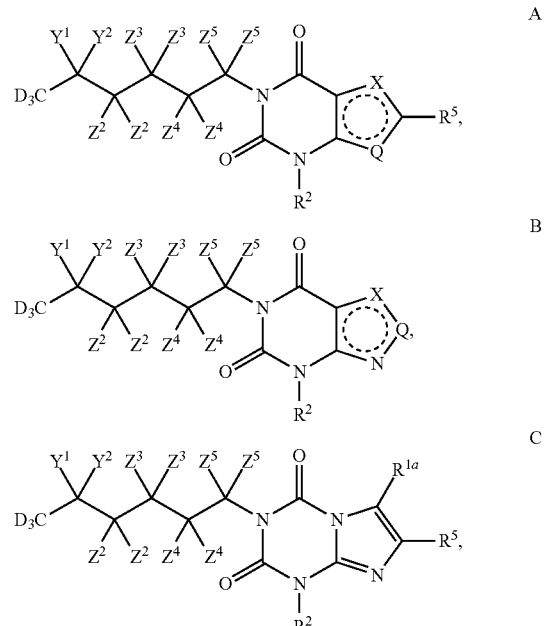

18 Claims, No Drawings

(56) References Cited

FOREIGN PATENT DOCUMENTS

| WO | 95/26325 A2 | 10/1995 |
|---|---|---|
| WO | 9605854 A2 | 2/1996 |
| WO | 2007041630 A1 | 4/2007 |
| WO | 2007/118651 A1 | 10/2007 |
| WO | 2009/108375 A1 | 9/2009 |
| WO | 2009/108383 A2 | 9/2009 |
| WO | 2011/028835 A1 | 3/2011 |
| WO | 2011/028922 A1 | 3/2011 |

OTHER PUBLICATIONS

Raoul, et al., A Novel Drug Interaction Between the Quinolone Antibiotic Ciprofloxacin and a Chiral Metabolite of Pentoxifylline, Biochemical Pharmacology; 74:639-646 (2007).

Anderson, R.J., "Recent Advances and developments in the treatment of acute renal failure," Expert Opin. Ther. Patents,vol. 12, No. 5, pp. 645-655, 2002.

Baillie, Thomas A., "The Use of Stable Isotopes in Pharmacological Research", Pharmacological Reviews, vol. 33, No. 2, pp. 81-132, 1981.

Browne, Thomas R., "Stable Isotope Techniques in Early Drug Development: An Economic Evaluation", J. Clin. Pharmacol, vol. 38, pp. 213-220, 1998.

Bursten, et al., "Lisofylline Causes Rapid and Prolonged Suppression of Serum Levels of Free Fatty Acids", The Journal of Pharmacology and Experimental Therapeutics, vol. 284, No. 1, pp. 337-345, 1997.

Cherrah, et al., "Study of Deuterium Isotope Effects on Protein Binding by Gas Chromatography/Mass Spectrometry. Caffeine and Deuterated Isotopomers", Biomedical and Environmental Mass Spectrometry, vol. 14, pp. 653-657, 1987.

Davis, et al., "Microbial models of mammalian metabolism: stereospecificaity of ketone reduction with pentoxifylline", Xenobiotica, vol. 15, No. 12, pp. 1001-1010, 1985.

Dyck, et al., "Effects of Deuterium Substitution on the Catabolism of ?-Phenylethylamine: An In Vivo Study", Journal of Neurochemistry, vol. 46, No. 2, pp. 399-404, 1986.

Ellermann, et al., Effect of pentoxifylline on the ischemic rat kidney monitored by 31P NMR spectroscopy in vivo, Biomed. Biochim. Acta, vol. 47, No. 6, pp. 515-521, 1988.

Fisher, et al., "The complexities inherent in attempts to decrease drug clearance by blocking sites of CYP-mediated metabolism," Current Opinion in Drug Discovery & Development, vol. 9, No. 1, pp. 101-109, 2006.

Foster, Allan B., "Deuterium isotope effects in studies of drug metabolism", TIPS, pp. 524-527, 1984.

Foster, Allan B., "Deuterium Isotope Effects in the Metabolism of Drugs and Xenobiotics: Implications for Drug Design", Advances in Drug Research, vol. 14, pp. 2-40, 1985.

Gouyette, et al., "Synthesis of Deuterium-labelled Elliptinium and its Use in Metabolic Studies", Biomedical and Environmental Mass Spectrometry, vol. 15, pp. 243-247, 1988.

Haskins, N.J., "The Application of Stable Isotopes in Biomedical Research", Biomedical Mass Spectrometry, vol. 9, No. 7, pp. 269-277, 1982.

Honma, et al., "Liberation of Deuterium from the Piperidine Ring during Hydroxylation", Drug Metabolism and Disposition, vol. 15, No. 4, pp. 551-559, 1987.

Kushner, et al., "Pharmacological uses and perspectives of heavy water and deuterated compounds", Can. J. Physiol. Pharmacol., vol. 77, pp. 79-88, 1999.

Lee et al., "Cytochrome P450 Isozymes Involved in Lisofylline Metabolism to Pentoxifylline in Human Liver Microsomes", Drug Metabolism and Disposition, vol. 25, No. 12, pp. 1354-1358, 1997.

Lillibridge, et al., "Metabolism of Lisofylline and Pentoxifylline in Human Liver Microsomes and Cytosol", Drug Metabolism and Disposition, vol. 24, No. 11, pp. 1174-1179, 1996.

Lin et al. "The Renoprotective Potential of Pentoxifylline in Chronic Kidney Disease," J. Chen. Med. Assoc. vol. 68, No. 3, pp. 99-105, 2005.

Paap, et al., "Multiple-Dose Pharmacokinetics of Pentoxifylline and its Metabolites During Renal Insufficiency", The Annals of Pharmacotherapy, vol. 30, pp. 724-729, 1996.

Park, et al. "Metabolism of Fluorine-containing Drugs," Annu. Rev. Pharmacol. Toxicol. (41) 443-70 (2001).

Pieniaszek, et al., "Moricizine Bioavailablity via Simultaneous, Dual, Stable Isotope Administration: Bioequivalence Implications", The Journal of Clinical Pharmacology, vol. 39, pp. 817-825, 1999.

Synfine Catalogue "Pentoxifylline-d3" listed in online catalogue dated Oct 21, 2007; accessed at http://web.archive.org/web/20071021050605/http://synfine.com/products_details.cfm?autoid=604.

Synfine Catalogue "1-(3-carboxypropyl) 3,7-dimethyl Xanthine-d6" listed in online catalogue dated Oct. 21, 2007; accessed at http://web.archive.org/web/20071021050610/http://synfine.com/products_details.cfm?autoid=605.

Synfine Catalogue "Hydroxy Pentoxifylline-d3" listed in online catalogue dated Oct 21, 2007; accessed at http://web.archive.org/web/20071021050615/http://synfine.com/products_details.cfm?autoid=606.

Ward et al. "Pentoxifylline. A review of its pharmacodynamic and pharmacokinetic properties and its therapeutic effects", Drugs, vol. 34, pp. 50-97, 1987.

Wolen, Robert L., "The Application of Stable Isotopes to Studies of Drug Bioabailablity and Bioequivalence", The Journal of Clinical Pharmacology, vol. 26, pp. 419-424, 1986.

Wyska, et al., "Pharmacokinetic modeling of pentoxifylline and lisofylline after oral and intravenous administration in mice", Journal of Pharmacy and Pharmacology, vol. 59, pp. 495-501, 2007.

Tonn, et al., Simultaneous Analysis of Diphenhydramine and a Stable Isotope Analog (2H10)Diphenhydramine Using Capillary Gas Chromatography with Mass Selective Detection in Biological Fluids from chronically Instrumented Pregnant Ewes, Biological Mass Spectrometry, vol. 22. 633-642, 1993.

International Search Report issued in PCT Application No. PCT/US2009/001294 on Jul. 8, 2009.

International Search Report issued in PCT Application No. PCT/US2009/001305 on Aug. 18, 2009.

International Search Report issued in PCT Application No. PCT/US2010/047574 on Oct. 14, 2010.

International Search Report issued in PCT Application No. PCT/US2010/047708 on Oct. 22, 2010.

International Preliminary Report on Patentabilty issued in PCT Application No. PCT/US2009/001305 on Aug. 31, 2010.

International Preliminary Report on Patentabilty issued in PCT Application No. PCT/US2009/001294 on Aug. 31, 2010.

Davila-Esqueda, M.E., et al., Pentofxifyline Diminishes the Oxidative Damage to Renal Tissue Induced by Streptozotocin in the Rat, Experimental Diab. Res., 5:245-251, 2004.

Friese, Ryan S., et al, Matrix Metalloproteinases: Discrete Elevations in Essential Hypertension and Hypertensive end-Stage Renal Disease, Clin. Exp. Hypertens, 31(7):521-533: Oct. 2009.

Cirillo, Pietro, et al., Systemic Inflammation, Metabolic Syndrome and Progressive Renal Disease, Nephrol Dial Transplant, 24:1384-1387, Feb. 10, 2009.

Tesch, Greg H., et al., Methods in Renal Research, Rodent Models of Streptozoticin-Induced Diabetic Nephropathy, Nephrology, 12:261-266, 2007.

Hewitson, Tim D., et al., Small Animal Models of Kidney Disease: A Review, Methods in Molecular Biology, 466:41-57, 2009.

Latta, Paul P., Pat. App. Lexis 4112, Board of Patent Appeals and Interference, 5pp, Oct. 10, 2007.

Saishin Souyaku Kagaku (The Practice of Medicinal Chemistry), Vi 1, p. 379, 1998.

Diabetic Nephropathy Treatment Overview, http://diabetes.webmd.com/tc/diabetic-nephropathy-treatment-overview, downloaded from the internet Jan. 16, 2013.

Written Opinion of the International Searching Authority issued in PCT/US2010/047574 dated Oct. 9, 2010.

Written Opinion of the International Searching Authority issued in PCT/US2010/047708 dated Oct. 9, 2010.

International Preliminary Report on Patentabilty issued in PCT Application No. PCT/US2010/047574 on Mar. 6, 2012.

(56) References Cited

OTHER PUBLICATIONS

International Preliminary Report on Patentabilty issued in PCT Application No. PCT/US2010/047708 on Mar. 6, 2012.
"Cell Therapeutics suffers on lisofylline trial data, cuts development" <http://www.thepharmaletter.com/file/20592/cell-therapeutics-suffers-on-lisofylline-trial-data-cuts-development,html> downloaded from the Internet Aug. 9, 2011.
Forbes et al., "Oxidative Stress as a Major Culprit in Kidney Disease in Diabetes," Diabetes, 57:1446-1454 (2008).
Magnusson et al. "Effects of pentoxifylline and its metabolites on platelet aggregation in whole blood from healthy humans," European Journal of Pharmacology 581:290-295 (2008).
Sweeney and McAuley, "Pharmacological Therapy for Acute Lung Injury," The Open Critical Care Medical Journal, 3:7-19 (2010).
TRENTAL FDA label, Aventis Pharmaceuticals Inc., Apr. 2004.
Written Opinion of the International Searching Authority issued in PCT/US2009/001294 dated Jul. 8, 2009.
Written Opinion of the International Searching Authority issued in PCT/US2009/001305 dated Aug. 18, 2009.
Cui, et al., In Synthesis and Biological Evaluation of Lisofylline (LSF) Analogs as a Potential Treatment for Type 1 Diabetes, Bioorganic Medicinal Chemistry Letters, vol. 16, pp. 3202 and 3401-3405, 2006.
Bolick, D., Lisofylline, a Novel Antiinflammatory Compound, Protects Mesangial Cells from Hyperglycemia-and Angiotensin II-Mediated Extracellular Matrix Deposition, Endocrinology 144, 12:5227-5231, 2003.
Buteau, K., Deuterated Drugs: Unexpectedly Nonobvious, J. High Tech. Law, 10:22-74, 2009.

\* cited by examiner

SUBSTITUTED DERIVATIVES OF BICYCLIC [4.3.0] HETEROARYL COMPOUNDS

RELATED APPLICATIONS

This application is the U.S. National Stage filed under 35 USC 371 of PCT/US2010/047557, filed Sep. 1, 2010, which claims the benefit of U.S. Provisional Application No. 61/239,371, filed on Sep. 2, 2009, the entire teachings of which are incorporated herein.

BACKGROUND OF THE INVENTION

Background of the Invention

Many current medicines suffer from poor absorption, distribution, metabolism and/or excretion (ADME) properties that prevent their wider use. Poor ADME properties are also a major reason for the failure of drug candidates in clinical trials. While formulation technologies and prodrug strategies can be employed in some cases to improve certain ADME properties, these approaches have failed to overcome the inherent ADME problems that exist for many drugs and drug candidates. One inherent problem is the rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems, such as poor patient compliance with the dosing regimen, side effects that become more acute with higher doses, and increased cost of treatment.

In some select cases, a metabolic inhibitor will be co-administered with an important drug that is rapidly cleared. Such is the case with the protease inhibitor class of drugs that are used to treat HIV infection. These drugs are typically co-dosed with ritonavir, an inhibitor of cytochrome P450 enzyme CYP3A4, the enzyme responsible for their metabolism. Ritonavir itself has side effects and it adds to the pill burden for HIV patients who must already take a combination of different drugs. Similarly, dextromethorphan which undergoes rapid CYP2D6 metabolism is being tested in combination with the CYP2D6 inhibitor quinidine for the treatment of pseudobulbar disease.

In general, combining drugs with cytochrome P450 inhibitors is not a satisfactory strategy for decreasing drug clearance. The inhibition of a CYP enzyme activity can affect the metabolism and clearance of other drugs metabolized by that same enzyme. This can cause those other drugs to accumulate in the body to toxic levels.

A potentially attractive strategy, if it works, for improving a drug's metabolic properties is deuterium modification. In this approach, one attempts to slow the CYP-mediated metabolism of a drug by replacing one or more hydrogen atoms with deuterium atoms. Deuterium is a safe, stable, non-radioactive isotope of hydrogen. Deuterium forms stronger bonds with carbon than hydrogen does. In select cases, the increased bond strength imparted by deuterium can positively impact the ADME properties of a drug, creating the potential for improved drug efficacy, safety, and tolerability. At the same time, because the size and shape of deuterium are essentially identical to hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, AB, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated decreased metabolic clearance. The variability in deuterium effects has also led experts to question or dismiss deuterium modification as a viable drug design strategy for inhibiting adverse metabolism. (See Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its undeuterated counterpart. Many drugs have multiple sites where metabolism is possible. The site(s) where deuterium substitution is required and the extent of deuteration necessary to see an effect on metabolism, if any, will be different for each drug.

SUMMARY OF THE INVENTION

This invention relates to novel compounds that are substituted derivatives of bicyclic [4.3.0] heteroaryl compounds and pharmaceutically acceptable salts thereof. This invention also provides compositions comprising one or more compounds of this invention and a carrier.

DETAILED DESCRIPTION OF THE INVENTION

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of a bicyclic [4.3.0] heteroayl compound that is not isotopically labeled will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku, 1994, 66: 15; Gannes L Z et al., Comp Biochem Physiol Mol Integr Physiol, 1998, 119: 725. In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3340 (50.1% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above, the relative amount of such isotopologues in toto will be less than 49.9% of the compound.

The invention also provides salts of the compounds of the invention. A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen sulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

It is understood that the carbon atom that bears substituents $Y^1$ and $Y^2$ in Formula A, B, or C can be chiral in some instances (when $Y^1$, $Y^2$ and $R^3$ are different from one another) and in other instances it can be achiral (when at least two of $Y^1$, $Y^2$ and $R^3$ are the same). As such, chiral compounds of this invention can exist as either individual enantiomers, or as racemic or scalemic mixtures of enantiomers. Accordingly, a compound of the present invention will include racemic and scalemic enantiomeric mixtures, as well as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are well known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "Tert", "ᵗ", and "t-" each refer to tertiary. "US" refers to the United States of America.

The term "optionally substituted with deuterium" means that one or more hydrogen atoms in the referenced moiety or compound may be replaced with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula A:

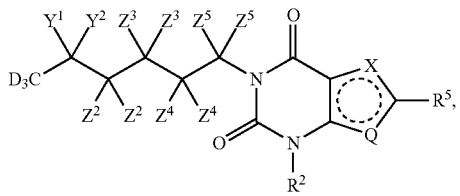

or a pharmaceutically acceptable salt thereof, wherein
each $Z^2$ is hydrogen or deuterium;
each $Z^3$ is hydrogen or deuterium;
each $Z^4$ is hydrogen or deuterium;
each $Z^5$ is hydrogen or deuterium;
the bicyclic ring system bearing X and Q is selected from:
(i) a 1H-pyrrolo[2,3-d]pyrimidine-2,4(3H,7H)-dione ring where X is $CR^{1a}$ and Q is $NR^7$, and
(ii) a 1H-pyrrolo[3,2-d]pyrimidine-2,4(3H,5H)-dione ring where X is $NR^1$ and Q is $CR^{1a}$;
either (a) $Y^1$ is OH, and $Y^2$ is hydrogen or deuterium, or (b) $Y^1$ and $Y^2$ are taken together with the carbon to which they are attached to form C=O;
$R^1$ is —$CH_3$ or —$CD_3$;
$R^{1a}$ is hydrogen, —$CH_3$ or —$CD_3$;
$R^2$ is —$CH_3$ or —$CD_3$;
$R^5$ is hydrogen or deuterium; and
$R^7$ is —$CH_3$, —$CD_3$, hydrogen or deuterium.

One embodiment of this invention relates to a compound of Formula A(i) wherein the bicyclic ring system bearing X and Q is a 1H-pyrrolo[2,3-d]pyrimidine-2,4(3H,7H)-dione ring:

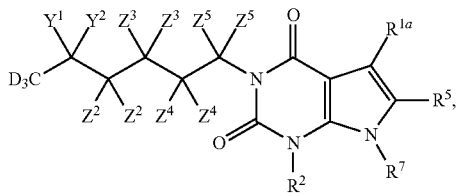

or a pharmaceutically acceptable salt thereof, where the Y, Z and R variables are as described above in Formula A. In one embodiment, $R^{1a}$ is $CH_3$. In another embodiment, $R^{1a}$ is $CD_3$. In another embodiment, $R^{1a}$ is hydrogen. In one embodiment, $R^2$ is $CH_3$. In another embodiment, $R^2$ is $CD_3$.

Another embodiment relates to a compound of Formula A(ii) wherein the bicyclic ring system bearing X and Q is a 1H-pyrrolo[3,2-d]pyrimidine-2,4(3H,5H)-dione ring:

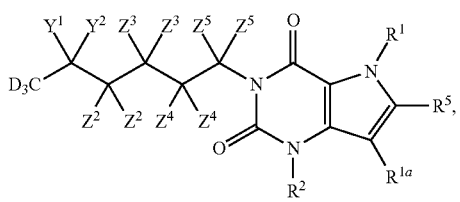

or a pharmaceutically acceptable salt thereof, where the Y, Z and R variables are as described above in Formula A. In one embodiment, $R^1$ is $CH_3$. In another embodiment, $R^1$ is $CD_3$.

In one embodiment, $R^5$ is hydrogen. In another embodiment, $R^5$ is deuterium. In one embodiment, $R^2$ is $CH_3$. In another embodiment, $R^2$ is $CD_3$.

As used herein, "a compound of Formula A" includes a compound of Formula A(i) and a compound of Formula A(ii).

The present invention also provides a compound of Formula B:

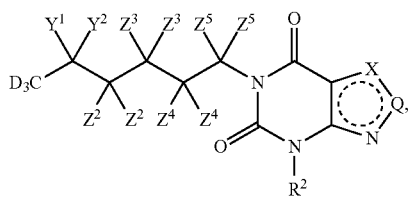

or a pharmaceutically acceptable salt thereof, wherein
each $Z^2$ is hydrogen or deuterium;
each $Z^3$ is hydrogen or deuterium;
each $Z^4$ is hydrogen or deuterium;
each $Z^5$ is hydrogen or deuterium;
the bicyclic ring system bearing X and Q is selected from:
(i) a 1H-[1,2,3]triazolo[4,5-d]pyrimidine-5,7(4H,6H)-dione ring where X is $NR^7$ and Q is N;
(ii) a 2H-[1,2,3]triazolo[4,5-d]pyrimidine-5,7(4H,6H)-dione ring where X is N and Q is $NR^1$;
and
(iii) a [1,2,5]thiadiazolo[3,4-d]pyrimidine-5,7(4H,6H)-dione ring where X is N and Q is S;
either (a) $Y^1$ is OH, and $Y^2$ is hydrogen or deuterium, or (b) $Y^1$ and $Y^2$ are taken together with the carbon to which they are attached to form C=O;
$R^1$ is —$CH_3$ or —$CD_3$;
$R^2$ is —$CH_3$ or —$CD_3$;
and
$R^7$ is $R^1$, hydrogen or deuterium.

One embodiment of this invention relates to a compound of Formula B(i) wherein the bicyclic ring system bearing X and Q is a 1H-[1,2,3]triazolo[4,5-d]pyrimidine-5,7(4H,6H)-dione ring

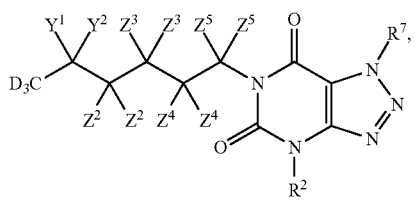

or a pharmaceutically acceptable salt thereof, where the Y, Z and R variables are as described above in Formula B. In one embodiment, $R^7$ is $R^1$. In one aspect of this embodiment, $R^1$ is $CH_3$. In another aspect of this embodiment, $R^1$ is $CD_3$. In one embodiment, $R^7$ is hydrogen. In another embodiment, $R^7$ is deuterium. In one embodiment, $R^2$ is $CH_3$. In another embodiment, $R^2$ is $CD_3$.

One embodiment of this invention relates to a compound of Formula B(ii) wherein the bicyclic ring system bearing X and Q is a 2H-[1,2,3]triazolo[4,5-d]pyrimidine-5,7(4H,6H)-dione ring:

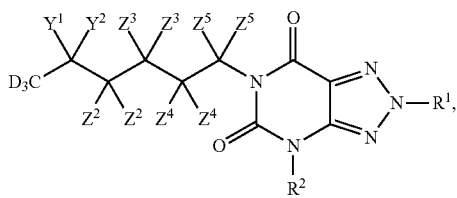

B(ii)

or a pharmaceutically acceptable salt thereof, where the Y, Z and R variables are as described above in Formula B. In one embodiment, $R^1$ is $CH_3$. In another embodiment, $R^1$ is $CD_3$. In one embodiment, $R^2$ is $CH_3$. In another embodiment, $R^2$ is $CD_3$.

One embodiment of this invention relates to a compound of Formula B(iii) wherein the bicyclic ring system bearing X and Q is a [1,2,5]thiadiazolo[3,4-d]pyrimidine-5,7(4H,6H)-dione ring:

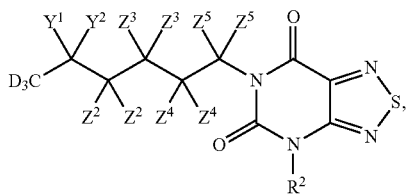

B(iii)

or a pharmaceutically acceptable salt thereof, where the Y, Z and R variables are as described above in Formula B. In one embodiment, $R^2$ is $CH_3$. In another embodiment, $R^2$ is $CD_3$.

As used herein, "a compound of Formula B" includes a compound of Formula B(i), a compound of Formula B(ii) and a compound of Formula B(iii).

The present invention also provides a compound of Formula C:

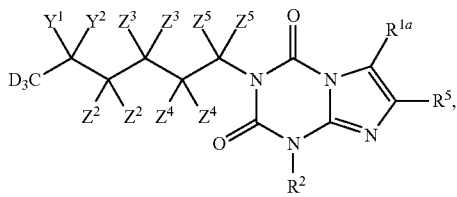

C or a pharmaceutically acceptable salt thereof, wherein
each $Z^2$ is hydrogen or deuterium;
each $Z^3$ is hydrogen or deuterium;
each $Z^4$ is hydrogen or deuterium;
each $Z^5$ is hydrogen or deuterium;
either (a) $Y^1$ is OH, and $Y^2$ is hydrogen or deuterium, or (b) $Y^1$ and $Y^2$ are taken together with the carbon to which they are attached to form C=O;
$R^{1a}$ is hydrogen, —$CH_3$ or —$CD_3$;
$R^2$ is —$CH_3$ or —$CD_3$; and
$R^5$ is hydrogen or deuterium.

In one embodiment, $R^{1a}$ is $CH_3$. In another embodiment, $R^{1a}$ is $CD_3$. In one embodiment, $R^5$ is hydrogen. In one embodiment, $R^5$ is deuterium. In one embodiment, $R^2$ is $CH_3$. In another embodiment, $R^2$ is $CD_3$.

One embodiment provides a compound of Formula A, B, or C, wherein each $Z^2$, $Z^3$, $Z^4$ and $Z^5$ is hydrogen. In one aspect, $Y^1$ and $Y^2$ are taken together with the carbon to which they are attached to form C=O. In another aspect, $Y^1$ is OH, and $Y^2$ is hydrogen or deuterium.

Another embodiment provides a compound of Formula A, B, or C, wherein each $Z^2$, $Z^3$, $Z^4$ and $Z^5$ is deuterium. In one aspect, $Y^1$ and $Y^2$ are taken together with the carbon to which they are attached to form C=O. In another aspect, $Y^1$ is OH, and $Y^2$ is hydrogen or deuterium.

Another embodiment provides a compound of Formula A, B, or C, wherein $Z^2$ is deuterium and either each of $Z^3$, $Z^4$ and $Z^5$ is hydrogen or each of $Z^3$, $Z^4$ and $Z^5$ is deuterium. In one aspect, $Y^1$ and $Y^2$ are taken together with the carbon to which they are attached to form C=O. In another aspect, $Y^1$ is OH, and $Y^2$ is hydrogen or deuterium.

A further embodiment provides a compound of Formula A, B, or C, wherein $Y^1$ and $Y^2$ are taken together with the carbon to which they are attached to form C=O. A still further embodiment provides a compound of Formula A, B, or C, wherein $Y^1$ is OH, and $Y^2$ is hydrogen or deuterium.

Specific examples of compounds of Formula A, B and C include those shown in Tables 1-8 (below) or pharmaceutically acceptable salts thereof

TABLE 1

Examples of Specific Compounds of Formula A(i) wherein $R^7$ is hydrogen. In the following table, $Z^3$, $Z^4$, and $Z^5$ are each hydrogen.

| Compound | $R^{1a}$ | $R^2$ | $R^5$ | $Z^2$ | $Y^1$ | $Y^2$ |
|---|---|---|---|---|---|---|
| 100 | $CH_3$ | $CH_3$ | H | H | taken together as =O | |
| 101 | $CD_3$ | $CH_3$ | H | H | taken together as =O | |
| 102 | $CH_3$ | $CD_3$ | H | H | taken together as =O | |
| 103 | $CD_3$ | $CD_3$ | H | H | taken together as =O | |
| 104 | $CH_3$ | $CH_3$ | H | D | taken together as =O | |
| 105 | $CD_3$ | $CH_3$ | H | D | taken together as =O | |
| 106 | $CH_3$ | $CD_3$ | H | D | taken together as =O | |
| 107 | $CD_3$ | $CD_3$ | H | D | taken together as =O | |
| 108 | $CH_3$ | $CH_3$ | D | H | taken together as =O | |
| 109 | $CD_3$ | $CH_3$ | D | H | taken together as =O | |
| 110 | $CH_3$ | $CD_3$ | D | H | taken together as =O | |
| 111 | $CD_3$ | $CD_3$ | D | H | taken together as =O | |
| 112 | $CH_3$ | $CH_3$ | D | D | taken together as =O | |
| 113 | $CD_3$ | $CH_3$ | D | D | taken together as =O | |
| 114 | $CH_3$ | $CD_3$ | D | D | taken together as =O | |
| 115 | $CD_3$ | $CD_3$ | D | D | taken together as =O | |
| 116 | $CH_3$ | $CH_3$ | H | H | OH | H |
| 117 | $CD_3$ | $CH_3$ | H | H | OH | H |
| 118 | $CH_3$ | $CD_3$ | H | H | OH | H |
| 119 | $CD_3$ | $CD_3$ | H | H | OH | H |
| 120 | $CH_3$ | $CH_3$ | H | D | OH | H |
| 121 | $CD_3$ | $CH_3$ | H | D | OH | H |
| 122 | $CH_3$ | $CD_3$ | H | D | OH | H |
| 123 | $CD_3$ | $CD_3$ | H | D | OH | H |
| 124 | $CH_3$ | $CH_3$ | D | H | OH | H |
| 125 | $CD_3$ | $CH_3$ | D | H | OH | H |
| 126 | $CH_3$ | $CD_3$ | D | H | OH | H |
| 127 | $CD_3$ | $CD_3$ | D | H | OH | H |
| 128 | $CH_3$ | $CH_3$ | D | D | OH | H |
| 129 | $CD_3$ | $CH_3$ | D | D | OH | H |
| 130 | $CH_3$ | $CD_3$ | D | D | OH | H |
| 131 | $CD_3$ | $CD_3$ | D | D | OH | H |
| 132 | $CH_3$ | $CH_3$ | H | H | OH | D |
| 133 | $CD_3$ | $CH_3$ | H | H | OH | D |
| 134 | $CH_3$ | $CD_3$ | H | H | OH | D |
| 135 | $CD_3$ | $CD_3$ | H | H | OH | D |
| 136 | $CH_3$ | $CH_3$ | H | D | OH | D |
| 137 | $CD_3$ | $CH_3$ | H | D | OH | D |
| 138 | $CH_3$ | $CD_3$ | H | D | OH | D |
| 139 | $CD_3$ | $CD_3$ | H | D | OH | D |
| 140 | $CH_3$ | $CH_3$ | D | H | OH | D |
| 141 | $CD_3$ | $CH_3$ | D | H | OH | D |
| 142 | $CH_3$ | $CD_3$ | D | H | OH | D |
| 143 | $CD_3$ | $CD_3$ | D | H | OH | D |
| 144 | $CH_3$ | $CH_3$ | D | D | OH | D |

TABLE 1-continued

Examples of Specific Compounds of Formula A(i) wherein $R^7$ is hydrogen. In the following table, $Z^3$, $Z^4$, and $Z^5$ are each hydrogen.

| Compound | $R^{1a}$ | $R^2$ | $R^5$ | $Z^2$ | $Y^1$ | $Y^2$ |
|---|---|---|---|---|---|---|
| 145 | $CD_3$ | $CH_3$ | D | D | OH | D |
| 146 | $CH_3$ | $CD_3$ | D | D | OH | D |
| 147 | $CD_3$ | $CD_3$ | D | D | OH | D |

TABLE 2

Examples of Specific Compounds of Formula A(i) wherein $R^7$ is $CH_3$ or $CD_3$ as indicated in the table. In the following table, $Z^3$, $Z^4$, and $Z^5$ are each hydrogen

| Compound | $R^7$ | $R^{1a}$ | $R^2$ | $R^5$ | $Z^2$ | $Y^1$ | $Y^2$ |
|---|---|---|---|---|---|---|---|
| 200 | $CH_3$ | H | $CH_3$ | H | H | taken together as =O | |
| 201 | $CD_3$ | H | $CH_3$ | H | H | taken together as =O | |
| 202 | $CH_3$ | H | $CD_3$ | H | H | taken together as =O | |
| 203 | $CD_3$ | H | $CD_3$ | H | H | taken together as =O | |
| 204 | $CH_3$ | H | $CH_3$ | H | D | taken together as =O | |
| 205 | $CD_3$ | H | $CH_3$ | H | D | taken together as =O | |
| 206 | $CH_3$ | H | $CD_3$ | H | D | taken together as =O | |
| 207 | $CD_3$ | H | $CD_3$ | H | D | taken together as =O | |
| 208 | $CH_3$ | H | $CH_3$ | D | H | taken together as =O | |
| 209 | $CD_3$ | H | $CH_3$ | D | H | taken together as =O | |
| 210 | $CH_3$ | H | $CD_3$ | D | H | taken together as =O | |
| 211 | $CD_3$ | H | $CD_3$ | D | H | taken together as =O | |
| 212 | $CH_3$ | H | $CH_3$ | D | D | taken together as =O | |
| 213 | $CD_3$ | H | $CH_3$ | D | D | taken together as =O | |
| 214 | $CH_3$ | H | $CD_3$ | D | D | taken together as =O | |
| 215 | $CD_3$ | H | $CD_3$ | D | D | taken together as =O | |
| 216 | $CH_3$ | H | $CH_3$ | H | H | OH | H |
| 217 | $CD_3$ | H | $CH_3$ | H | H | OH | H |
| 218 | $CH_3$ | H | $CD_3$ | H | H | OH | H |
| 219 | $CD_3$ | H | $CD_3$ | H | H | OH | H |
| 220 | $CH_3$ | H | $CH_3$ | H | D | OH | H |
| 221 | $CD_3$ | H | $CH_3$ | H | D | OH | H |
| 222 | $CH_3$ | H | $CD_3$ | H | D | OH | H |
| 223 | $CD_3$ | H | $CD_3$ | H | D | OH | H |
| 224 | $CH_3$ | H | $CH_3$ | D | H | OH | H |
| 225 | $CD_3$ | H | $CH_3$ | D | H | OH | H |
| 226 | $CH_3$ | H | $CD_3$ | D | H | OH | H |
| 227 | $CD_3$ | H | $CD_3$ | D | H | OH | H |
| 228 | $CH_3$ | H | $CH_3$ | D | D | OH | H |
| 229 | $CD_3$ | H | $CH_3$ | D | D | OH | H |
| 230 | $CH_3$ | H | $CD_3$ | D | D | OH | H |
| 231 | $CD_3$ | H | $CD_3$ | D | D | OH | H |
| 232 | $CH_3$ | H | $CH_3$ | H | H | OH | D |
| 233 | $CD_3$ | H | $CH_3$ | H | H | OH | D |
| 234 | $CH_3$ | H | $CD_3$ | H | H | OH | D |
| 235 | $CD_3$ | H | $CD_3$ | H | H | OH | D |
| 236 | $CH_3$ | H | $CH_3$ | H | D | OH | D |
| 237 | $CD_3$ | H | $CH_3$ | H | D | OH | D |
| 238 | $CH_3$ | H | $CD_3$ | H | D | OH | D |
| 239 | $CD_3$ | H | $CD_3$ | H | D | OH | D |
| 240 | $CH_3$ | H | $CH_3$ | D | H | OH | D |
| 241 | $CD_3$ | H | $CH_3$ | D | H | OH | D |
| 242 | $CH_3$ | H | $CD_3$ | D | H | OH | D |
| 243 | $CD_3$ | H | $CD_3$ | D | H | OH | D |
| 244 | $CH_3$ | H | $CH_3$ | D | D | OH | D |
| 245 | $CD_3$ | H | $CH_3$ | D | D | OH | D |
| 246 | $CH_3$ | H | $CD_3$ | D | D | OH | D |
| 247 | $CD_3$ | H | $CD_3$ | D | D | OH | D |
| 248 | $CH_3$ | $CD_3$ | $CH_3$ | H | H | taken together as =O | |
| 249 | $CD_3$ | $CD_3$ | $CH_3$ | H | H | taken together as =O | |
| 250 | $CH_3$ | $CD_3$ | $CD_3$ | H | H | taken together as =O | |
| 251 | $CD_3$ | $CD_3$ | $CD_3$ | H | H | taken together as =O | |
| 252 | $CH_3$ | $CD_3$ | $CH_3$ | H | D | taken together as =O | |
| 253 | $CD_3$ | $CD_3$ | $CH_3$ | H | D | taken together as =O | |
| 254 | $CH_3$ | $CD_3$ | $CD_3$ | H | D | taken together as =O | |
| 255 | $CD_3$ | $CD_3$ | $CD_3$ | H | D | taken together as =O | |
| 256 | $CH_3$ | $CD_3$ | $CH_3$ | D | H | taken together as =O | |
| 257 | $CD_3$ | $CD_3$ | $CH_3$ | D | H | taken together as =O | |
| 258 | $CH_3$ | $CD_3$ | $CD_3$ | D | H | taken together as =O | |

TABLE 2-continued

Examples of Specific Compounds of Formula A(i) wherein $R^7$ is $CH_3$ or $CD_3$ as indicated in the table. In the following table, $Z^3$, $Z^4$, and $Z^5$ are each hydrogen

| Compound | $R^7$ | $R^{1a}$ | $R^2$ | $R^5$ | $Z^2$ | $Y^1$ | $Y^2$ |
|---|---|---|---|---|---|---|---|
| 259 | $CD_3$ | $CD_3$ | $CD_3$ | D | H | taken together as =O | |
| 260 | $CH_3$ | $CD_3$ | $CH_3$ | D | D | taken together as =O | |
| 261 | $CD_3$ | $CD_3$ | $CH_3$ | D | D | taken together as =O | |
| 262 | $CH_3$ | $CD_3$ | $CD_3$ | D | D | taken together as =O | |
| 263 | $CD_3$ | $CD_3$ | $CD_3$ | D | D | taken together as =O | |
| 264 | $CH_3$ | $CD_3$ | $CH_3$ | H | H | OH | H |
| 265 | $CD_3$ | $CD_3$ | $CH_3$ | H | H | OH | H |
| 266 | $CH_3$ | $CD_3$ | $CD_3$ | H | H | OH | H |
| 267 | $CD_3$ | $CD_3$ | $CD_3$ | H | H | OH | H |
| 268 | $CH_3$ | $CD_3$ | $CH_3$ | H | D | OH | H |
| 269 | $CD_3$ | $CD_3$ | $CH_3$ | H | D | OH | H |
| 270 | $CH_3$ | $CD_3$ | $CD_3$ | H | D | OH | H |
| 271 | $CD_3$ | $CD_3$ | $CD_3$ | H | D | OH | H |
| 272 | $CH_3$ | $CD_3$ | $CH_3$ | D | H | OH | H |
| 273 | $CD_3$ | $CD_3$ | $CH_3$ | D | H | OH | H |
| 274 | $CH_3$ | $CD_3$ | $CD_3$ | D | H | OH | H |
| 275 | $CD_3$ | $CD_3$ | $CD_3$ | D | H | OH | H |
| 276 | $CH_3$ | $CD_3$ | $CH_3$ | D | D | OH | H |
| 277 | $CD_3$ | $CD_3$ | $CH_3$ | D | D | OH | H |
| 278 | $CH_3$ | $CD_3$ | $CD_3$ | D | D | OH | H |
| 279 | $CD_3$ | $CD_3$ | $CD_3$ | D | D | OH | H |
| 280 | $CH_3$ | $CD_3$ | $CH_3$ | H | H | OH | D |
| 281 | $CD_3$ | $CD_3$ | $CH_3$ | H | H | OH | D |
| 282 | $CH_3$ | $CD_3$ | $CD_3$ | H | H | OH | D |
| 283 | $CD_3$ | $CD_3$ | $CD_3$ | H | H | OH | D |
| 284 | $CH_3$ | $CD_3$ | $CH_3$ | H | D | OH | D |
| 285 | $CD_3$ | $CD_3$ | $CH_3$ | H | D | OH | D |
| 286 | $CH_3$ | $CD_3$ | $CD_3$ | H | D | OH | D |
| 287 | $CD_3$ | $CD_3$ | $CD_3$ | H | D | OH | D |
| 288 | $CH_3$ | $CD_3$ | $CH_3$ | D | H | OH | D |
| 289 | $CD_3$ | $CD_3$ | $CH_3$ | D | H | OH | D |
| 290 | $CH_3$ | $CD_3$ | $CD_3$ | D | H | OH | D |
| 291 | $CD_3$ | $CD_3$ | $CD_3$ | D | H | OH | D |
| 292 | $CH_3$ | $CD_3$ | $CH_3$ | D | D | OH | D |
| 293 | $CD_3$ | $CD_3$ | $CH_3$ | D | D | OH | D |
| 294 | $CH_3$ | $CD_3$ | $CD_3$ | D | D | OH | D |
| 295 | $CD_3$ | $CD_3$ | $CD_3$ | D | D | OH | D |

TABLE 3

Examples of Specific Compounds of Formula A(ii), wherein $Z^3$, $Z^4$, and $Z^5$ are each hydrogen.

| Compound | $R^1$ | $R^2$ | $R^5$ | $Z^2$ | $Y^1$ | $Y^2$ |
|---|---|---|---|---|---|---|
| 700 | $CH_3$ | $CH_3$ | H | H | taken together as =O | |
| 701 | $CD_3$ | $CH_3$ | H | H | taken together as =O | |
| 702 | $CH_3$ | $CD_3$ | H | H | taken together as =O | |
| 703 | $CD_3$ | $CD_3$ | H | H | taken together as =O | |
| 704 | $CH_3$ | $CH_3$ | H | D | taken together as =O | |
| 705 | $CD_3$ | $CH_3$ | H | D | taken together as =O | |
| 706 | $CH_3$ | $CD_3$ | H | D | taken together as =O | |
| 707 | $CD_3$ | $CD_3$ | H | D | taken together as =O | |
| 708 | $CH_3$ | $CH_3$ | D | H | taken together as =O | |
| 709 | $CD_3$ | $CH_3$ | D | H | taken together as =O | |
| 710 | $CH_3$ | $CD_3$ | D | H | taken together as =O | |
| 711 | $CD_3$ | $CD_3$ | D | H | taken together as =O | |
| 712 | $CH_3$ | $CH_3$ | D | D | taken together as =O | |
| 713 | $CD_3$ | $CH_3$ | D | D | taken together as =O | |
| 714 | $CH_3$ | $CD_3$ | D | D | taken together as =O | |
| 715 | $CD_3$ | $CD_3$ | D | D | taken together as =O | |
| 716 | $CH_3$ | $CH_3$ | H | H | OH | H |
| 717 | $CD_3$ | $CH_3$ | H | H | OH | H |
| 718 | $CH_3$ | $CD_3$ | H | H | OH | H |
| 719 | $CD_3$ | $CD_3$ | H | H | OH | H |
| 720 | $CH_3$ | $CH_3$ | H | D | OH | H |
| 721 | $CD_3$ | $CH_3$ | H | D | OH | H |
| 722 | $CH_3$ | $CD_3$ | H | D | OH | H |
| 723 | $CD_3$ | $CD_3$ | H | D | OH | H |
| 724 | $CH_3$ | $CH_3$ | D | H | OH | H |
| 725 | $CD_3$ | $CH_3$ | D | H | OH | H |

TABLE 3-continued

Examples of Specific Compounds of Formula A(ii), wherein $Z^3$, $Z^4$, and $Z^5$ are each hydrogen.

| Compound | $R^1$ | $R^2$ | $R^5$ | $Z^2$ | $Y^1$ | $Y^2$ |
|---|---|---|---|---|---|---|
| 726 | $CH_3$ | $CD_3$ | D | H | OH | H |
| 727 | $CD_3$ | $CD_3$ | D | H | OH | H |
| 728 | $CH_3$ | $CH_3$ | D | D | OH | H |
| 729 | $CD_3$ | $CH_3$ | D | D | OH | H |
| 730 | $CH_3$ | $CD_3$ | D | D | OH | H |
| 731 | $CD_3$ | $CD_3$ | D | D | OH | H |
| 732 | $CH_3$ | $CH_3$ | H | H | OH | D |
| 733 | $CD_3$ | $CH_3$ | H | H | OH | D |
| 734 | $CH_3$ | $CD_3$ | H | H | OH | D |
| 735 | $CD_3$ | $CD_3$ | H | H | OH | D |
| 736 | $CH_3$ | $CH_3$ | H | D | OH | D |
| 737 | $CD_3$ | $CH_3$ | H | D | OH | D |
| 738 | $CH_3$ | $CD_3$ | H | D | OH | D |
| 739 | $CD_3$ | $CD_3$ | H | D | OH | D |
| 740 | $CH_3$ | $CH_3$ | D | H | OH | D |
| 741 | $CD_3$ | $CH_3$ | D | H | OH | D |
| 742 | $CH_3$ | $CD_3$ | D | H | OH | D |
| 743 | $CD_3$ | $CD_3$ | D | H | OH | D |
| 744 | $CH_3$ | $CH_3$ | D | D | OH | D |
| 745 | $CD_3$ | $CH_3$ | D | D | OH | D |
| 746 | $CH_3$ | $CD_3$ | D | D | OH | D |
| 747 | $CD_3$ | $CD_3$ | D | D | OH | D |

TABLE 4

Examples of Specific Compounds of Formula B(i) wherein $R^7$ is hydrogen. In the following table, $Z^3$, $Z^4$, and $Z^5$ are each hydrogen.

| Compound | $R^2$ | $Z^2$ | $Y^1$ | $Y^2$ |
|---|---|---|---|---|
| 300 | $CH_3$ | H | taken together as =O | |
| 301 | $CD_3$ | H | taken together as =O | |
| 302 | $CH_3$ | D | taken together as =O | |
| 303 | $CD_3$ | D | taken together as =O | |
| 304 | $CH_3$ | H | OH | H |
| 305 | $CD_3$ | H | OH | H |
| 306 | $CH_3$ | D | OH | H |
| 307 | $CD_3$ | D | OH | H |
| 308 | $CH_3$ | H | OH | D |
| 309 | $CD_3$ | H | OH | D |
| 310 | $CH_3$ | D | OH | D |
| 311 | $CD_3$ | D | OH | D |

TABLE 5

Examples of Specific Compounds of Formula B(i). In the following table, $Z^3$, $Z^4$, and $Z^5$ are each hydrogen.

| Compound | $R^7$ | $R^2$ | $Z^2$ | $Y^1$ | $Y^2$ |
|---|---|---|---|---|---|
| 500 | $CH_3$ | $CH_3$ | H | taken together as =O | |
| 501 | $CD_3$ | $CH_3$ | H | taken together as =O | |
| 502 | $CH_3$ | $CD_3$ | H | taken together as =O | |
| 503 | $CD_3$ | $CD_3$ | H | taken together as =O | |
| 504 | $CH_3$ | $CH_3$ | D | taken together as =O | |
| 505 | $CD_3$ | $CH_3$ | D | taken together as =O | |
| 506 | $CH_3$ | $CD_3$ | D | taken together as =O | |
| 507 | $CD_3$ | $CD_3$ | D | taken together as =O | |
| 508 | $CH_3$ | $CH_3$ | H | OH | H |
| 509 | $CD_3$ | $CH_3$ | H | OH | H |
| 510 | $CH_3$ | $CD_3$ | H | OH | H |
| 511 | $CD_3$ | $CD_3$ | H | OH | H |
| 512 | $CH_3$ | $CH_3$ | D | OH | H |
| 513 | $CD_3$ | $CH_3$ | D | OH | H |
| 514 | $CH_3$ | $CD_3$ | D | OH | H |
| 515 | $CD_3$ | $CD_3$ | D | OH | H |
| 516 | $CH_3$ | $CH_3$ | H | OH | D |
| 517 | $CD_3$ | $CH_3$ | H | OH | D |
| 518 | $CH_3$ | $CD_3$ | H | OH | D |
| 519 | $CD_3$ | $CD_3$ | H | OH | D |
| 520 | $CH_3$ | $CH_3$ | D | OH | D |
| 521 | $CD_3$ | $CH_3$ | D | OH | D |
| 522 | $CH_3$ | $CD_3$ | D | OH | D |
| 523 | $CD_3$ | $CD_3$ | D | OH | D |

TABLE 6

Examples of Specific Compounds of Formula B(ii). In the following table, $Z^3$, $Z^4$, and $Z^5$ are each hydrogen.

| Compound | $R^1$ | $R^2$ | $Z^2$ | $Y^1$ | $Y^2$ |
|---|---|---|---|---|---|
| 600 | $CH_3$ | $CH_3$ | H | taken together as =O | |
| 601 | $CD_3$ | $CH_3$ | H | taken together as =O | |
| 602 | $CH_3$ | $CD_3$ | H | taken together as =O | |
| 603 | $CD_3$ | $CD_3$ | H | taken together as =O | |
| 604 | $CH_3$ | $CH_3$ | D | taken together as =O | |
| 605 | $CD_3$ | $CH_3$ | D | taken together as =O | |
| 606 | $CH_3$ | $CD_3$ | D | taken together as =O | |
| 607 | $CD_3$ | $CD_3$ | D | taken together as =O | |
| 608 | $CH_3$ | $CH_3$ | H | OH | H |
| 609 | $CD_3$ | $CH_3$ | H | OH | H |
| 610 | $CH_3$ | $CD_3$ | H | OH | H |
| 611 | $CD_3$ | $CD_3$ | H | OH | H |
| 612 | $CH_3$ | $CH_3$ | D | OH | H |
| 613 | $CD_3$ | $CH_3$ | D | OH | H |
| 614 | $CH_3$ | $CD_3$ | D | OH | H |
| 615 | $CD_3$ | $CD_3$ | D | OH | H |
| 616 | $CH_3$ | $CH_3$ | H | OH | D |
| 617 | $CD_3$ | $CH_3$ | H | OH | D |
| 618 | $CH_3$ | $CD_3$ | H | OH | D |
| 619 | $CD_3$ | $CD_3$ | H | OH | D |
| 620 | $CH_3$ | $CH_3$ | D | OH | D |
| 621 | $CD_3$ | $CH_3$ | D | OH | D |
| 622 | $CH_3$ | $CD_3$ | D | OH | D |
| 623 | $CD_3$ | $CD_3$ | D | OH | D |

TABLE 7

Examples of Specific Compounds of Formula B(iii). In the following table, $Z^3$, $Z^4$, and $Z^5$ are each hydrogen.

| Compound | $R^2$ | $Z^2$ | $Y^1$ | $Y^2$ |
|---|---|---|---|---|
| 400 | $CH_3$ | H | taken together as =O | |
| 401 | $CD_3$ | H | taken together as =O | |
| 402 | $CH_3$ | D | taken together as =O | |
| 403 | $CD_3$ | D | taken together as =O | |
| 404 | $CH_3$ | H | OH | H |
| 405 | $CD_3$ | H | OH | H |
| 406 | $CH_3$ | D | OH | H |
| 407 | $CD_3$ | D | OH | H |
| 408 | $CH_3$ | H | OH | D |
| 409 | $CD_3$ | H | OH | D |
| 410 | $CH_3$ | D | OH | D |
| 411 | $CD_3$ | D | OH | D |

TABLE 8

Examples of Specific Compounds of Formula C, wherein $Z^3$, $Z^4$, and $Z^5$ are each hydrogen.

| Compound | $R^{1a}$ | $R^2$ | $R^5$ | $Z^2$ | $Y^1$ | $Y^2$ |
|---|---|---|---|---|---|---|
| 800 | $CH_3$ | $CH_3$ | H | H | taken together as =O | |
| 801 | $CD_3$ | $CH_3$ | H | H | taken together as =O | |
| 802 | $CH_3$ | $CD_3$ | H | H | taken together as =O | |

TABLE 8-continued

Examples of Specific Compounds of Formula C, wherein $Z^3$, $Z^4$, and $Z^5$ are each hydrogen.

| Compound | $R^{1a}$ | $R^2$ | $R^5$ | $Z^2$ | $Y^1$ | $Y^2$ |
|---|---|---|---|---|---|---|
| 803 | $CD_3$ | $CD_3$ | H | H | taken together as =O | |
| 804 | $CH_3$ | $CH_3$ | H | D | taken together as =O | |
| 805 | $CD_3$ | $CH_3$ | H | D | taken together as =O | |
| 806 | $CH_3$ | $CD_3$ | H | D | taken together as =O | |
| 807 | $CD_3$ | $CD_3$ | H | D | taken together as =O | |
| 808 | $CH_3$ | $CH_3$ | D | H | taken together as =O | |
| 809 | $CD_3$ | $CH_3$ | D | H | taken together as =O | |
| 810 | $CH_3$ | $CD_3$ | D | H | taken together as =O | |
| 811 | $CD_3$ | $CD_3$ | D | H | taken together as =O | |
| 812 | $CH_3$ | $CH_3$ | D | D | taken together as =O | |
| 813 | $CD_3$ | $CH_3$ | D | D | taken together as =O | |
| 814 | $CH_3$ | $CD_3$ | D | D | taken together as =O | |
| 815 | $CD_3$ | $CD_3$ | D | D | taken together as =O | |
| 816 | $CH_3$ | $CH_3$ | H | H | OH | H |
| 817 | $CD_3$ | $CH_3$ | H | H | OH | H |
| 818 | $CH_3$ | $CD_3$ | H | H | OH | H |
| 819 | $CD_3$ | $CD_3$ | H | H | OH | H |
| 820 | $CH_3$ | $CH_3$ | H | D | OH | H |
| 821 | $CD_3$ | $CH_3$ | H | D | OH | H |
| 822 | $CH_3$ | $CD_3$ | H | D | OH | H |
| 823 | $CD_3$ | $CD_3$ | H | D | OH | H |
| 824 | $CH_3$ | $CH_3$ | D | H | OH | H |
| 825 | $CD_3$ | $CH_3$ | D | H | OH | H |
| 826 | $CH_3$ | $CD_3$ | D | H | OH | H |
| 827 | $CD_3$ | $CD_3$ | D | H | OH | H |
| 828 | $CH_3$ | $CH_3$ | D | D | OH | H |
| 829 | $CD_3$ | $CH_3$ | D | D | OH | H |
| 830 | $CH_3$ | $CD_3$ | D | D | OH | H |
| 831 | $CD_3$ | $CD_3$ | D | D | OH | H |
| 832 | $CH_3$ | $CH_3$ | H | H | OH | D |
| 833 | $CD_3$ | $CH_3$ | H | H | OH | D |
| 834 | $CH_3$ | $CD_3$ | H | H | OH | D |
| 835 | $CD_3$ | $CD_3$ | H | H | OH | D |
| 836 | $CH_3$ | $CH_3$ | H | D | OH | D |
| 837 | $CD_3$ | $CH_3$ | H | D | OH | D |
| 838 | $CH_3$ | $CD_3$ | H | D | OH | D |
| 839 | $CD_3$ | $CD_3$ | H | D | OH | D |
| 840 | $CH_3$ | $CH_3$ | D | H | OH | D |
| 841 | $CD_3$ | $CH_3$ | D | H | OH | D |
| 842 | $CH_3$ | $CD_3$ | D | H | OH | D |
| 843 | $CD_3$ | $CD_3$ | D | H | OH | D |
| 844 | $CH_3$ | $CH_3$ | D | D | OH | D |
| 845 | $CD_3$ | $CH_3$ | D | D | OH | D |
| 846 | $CH_3$ | $CD_3$ | D | D | OH | D |
| 847 | $CD_3$ | $CD_3$ | D | D | OH | D |

The invention is also directed to the compounds E(i)-E(xiii):

E(i), E(ii), E(iii), E(iv), E(v), E(vi), E(vii), E(viii), E(ix), E(x), X(xi), E(xii), E(xiii) [chemical structures]

In another set of embodiments, any atom not designated as deuterium in any of the embodiments set forth above is present at its natural isotopic abundance.

The synthesis of compounds of this invention can be achieved by synthetic chemists of ordinary skill with reference to the Schemes below.

Exemplary Synthesis

Exemplary methods for synthesizing compounds of Formula A, B, or C are depicted in the following schemes.

Scheme I. Synthesis of compounds of Formula A(i) wherein $Z^2$ is D.
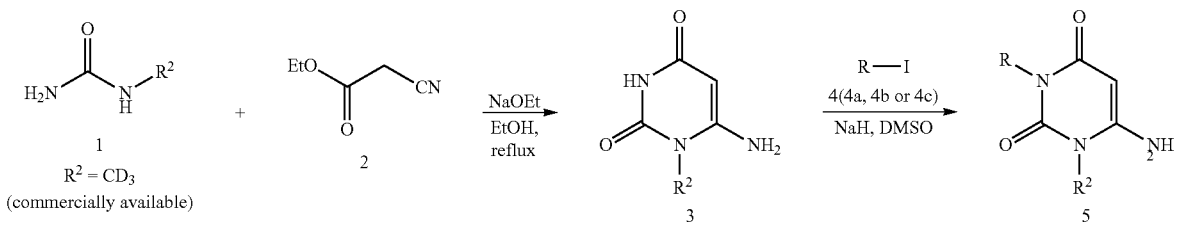
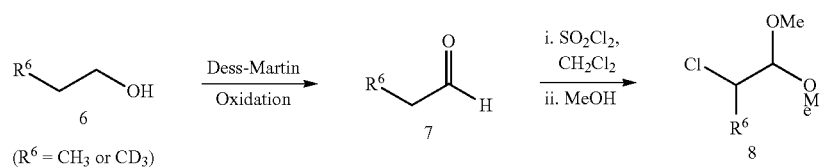
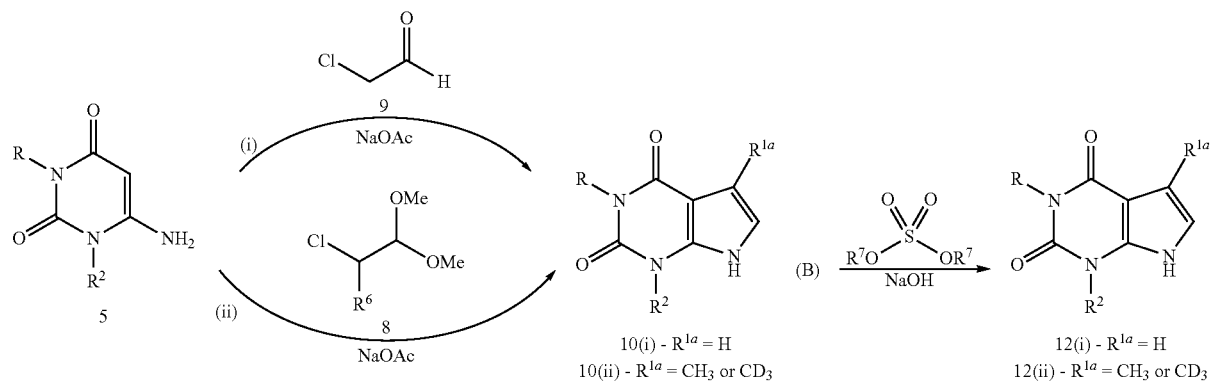
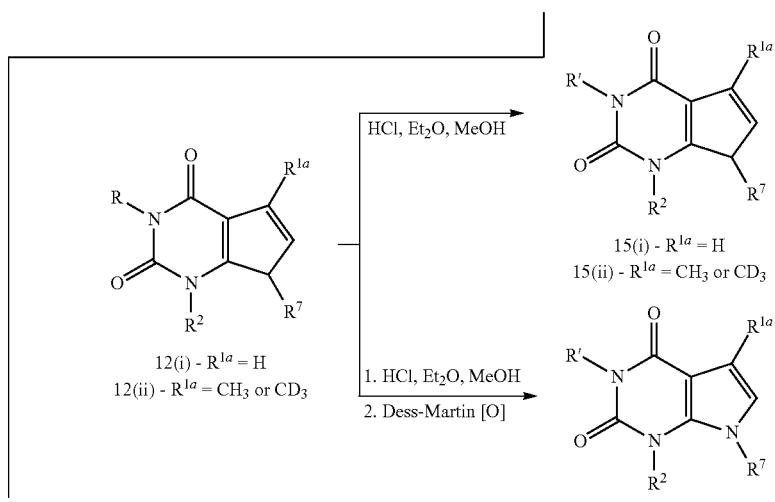

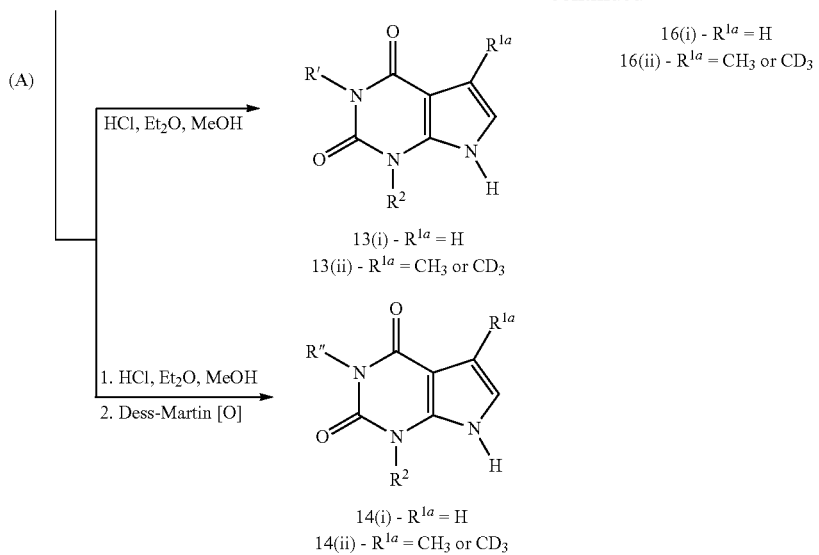
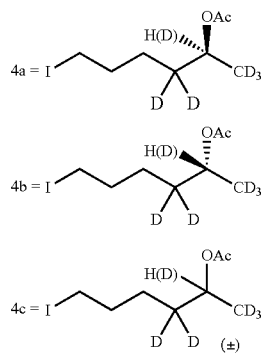
X = H or D
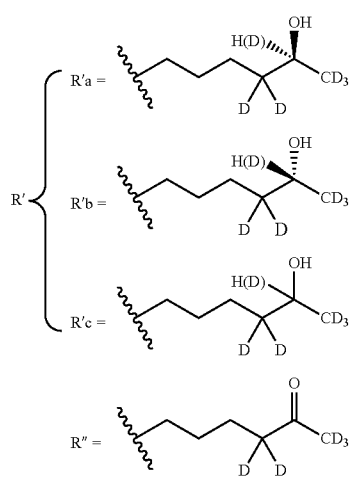

Scheme I shows an example of a synthesis of a compound of Formula A(i) wherein $Z^2$ is D and either (A) $R^7$ is hydrogen, or (B) $R^7$ is $CH_3$ or $CD_3$. As shown in Scheme I, commercially available trideuteromethylurea 1 is condensed with ethyl cyanoacetate 2 analogously to what is described by Elzein et al., J. Med. Chem. 2008, 51, 2269-78 to provide pyrimidinedione 3. N-alkylation of 3 with alkyl iodide R—I 4 in a manner analogous to what is described in U.S. Pat. No. 6,878,715, provides 5. As used in Scheme I and the Schemes below, 4 is used to denote 4a, 4b, or 4c, which represent respectively the (S) enantiomer, the (R) enantiomer, and the racemic mixture of the alkyl iodide, as also shown in Scheme I. Each of 4a, 4b and 4c may be prepared as described in Scheme VII below.

5 is now allowed to react with either (i) chloroacetaldehyde 9 in a manner analogous to the procedure of Haroka et al., Chem. Pharm. Bul. 1974, 22, 1459-67, to provide the 1H-pyrrolo[2,3-d]pyrimidine-2,4(3H,7H)-dione 10(i); or (ii) α-chloroacetal 8 to provide the 1H-pyrrolo[2,3-d]pyrimidine-2,4(3H,7H)-dione 10(ii). 8 is prepared as described in Scheme I by Dess-Martin oxidation of 6 to provide 7. 7 is then chlorinated with sulfuryl chloride and then treated with methanol to provide 8.

To provide a compound where $R^7$ is hydrogen, 10(i) and 10(ii) are treated (path (A)) with either HCl in methanol and ether to provide 13(i) and 13(ii), respectively, or with ethereal HCl in methanol followed by subsequent Dess-Martin oxidation to provide 14(i) and 14(ii), respectively. Both of the above alternative steps are conducted in a manner analogous to what is described in Cui et al., Biorg. Med. Chem. Lett. 2006, 16, 3401-05. In 13(i) and 13(ii), the group R' may be R'a, R'b, or R'c, each of which is defined in Scheme I. The definition of R' also applies to structures containing R' in the Schemes below. The stereochemical configuration of R'a, R'b and R'c in 13(i) and 13(ii), and in all structures that contain the group R' corresponds to the configuration of the R group in 4a, 4b, and 4c, respectively. In 14(i) and 14(ii), the group R" is defined in Scheme I. The definition of R" also applies to structures containing R" in the Schemes below.

To provide a compound where $R^7$ is $CH_3$ or $CD_3$, 10(i) and 10(ii) are alkylated (path (B)) with dialkylsulfate 11 to provide 12(i) and 12(ii), respectively. 12(i) and 12(ii) are then treated with either HCl in methanol and ether to provide 15(i) and 15(ii), respectively or with ethereal HCl in methanol followed by subsequent Dess-Martin oxidation to provide 16(i) and 16(ii), respectively.

Scheme II. Synthesis of compounds of Formula A(ii) wherein $Z^2$ is D.

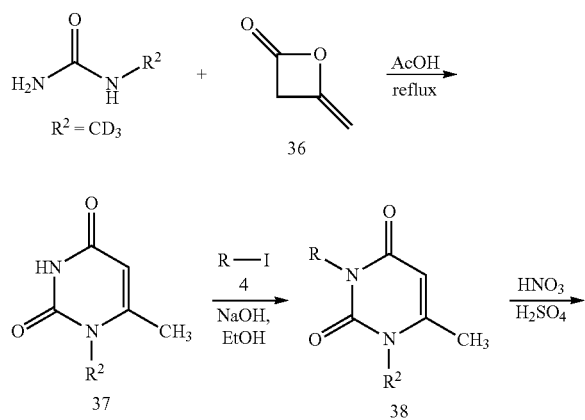

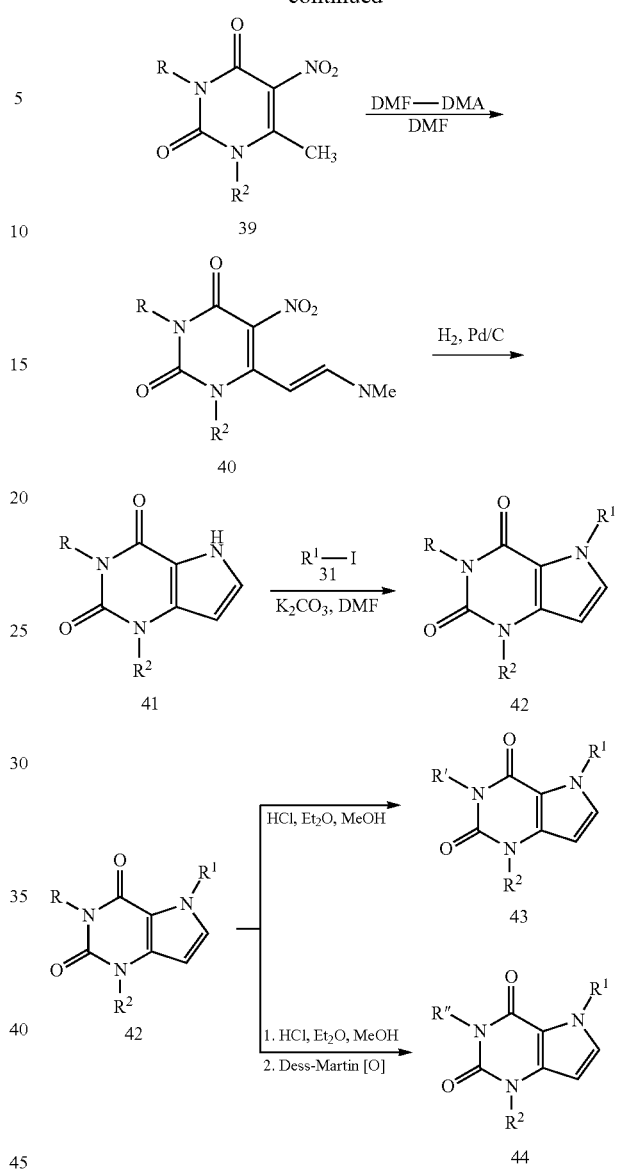

Scheme II shows an example of a synthesis of a compound of Formula A(ii) wherein $Z^2$ is D. Commercially available trideuteromethylurea 1 is condensed with diketene 36 analogously to what is described in Vidal et al., Biorg. Med. Chem. Lett. 2006, 16, 3642-45 to provide pyrimidinedione 37.

N-alkylation with 4 followed by nitration of the pyrimidinedione with nitric acid and sulfuric acid in a manner analogous to Vidal et al. provides pyrimidinedione 39. Condensation with dimethyl formamide-dimethylacetal analogously to what is described by Haroka et al., Chem. Pharm. Bul. 1974, 22, 2593-2598 provides enamine 40 which on treatment with $H_2$ and Pd/C undergoes reductive cyclization to 41. 41 is alkylated with $R^1$—I 31 in a manner analogous to Haroka et al. to provide 42, which is then treated with either HCl in methanol and ether to provide 43 or with ethereal HCl in methanol followed by subsequent Dess-Martin oxidation to provide 44. Both of the above alternative steps are conducted in a manner analogous to what is described in Cui et al., Biorg. Med. Chem. Lett. 2006, 16, 3401-05.

Scheme III. Synthesis of compounds of Formula B(i) wherein $R^7$ is hydrogen and $Z^2$ is D.

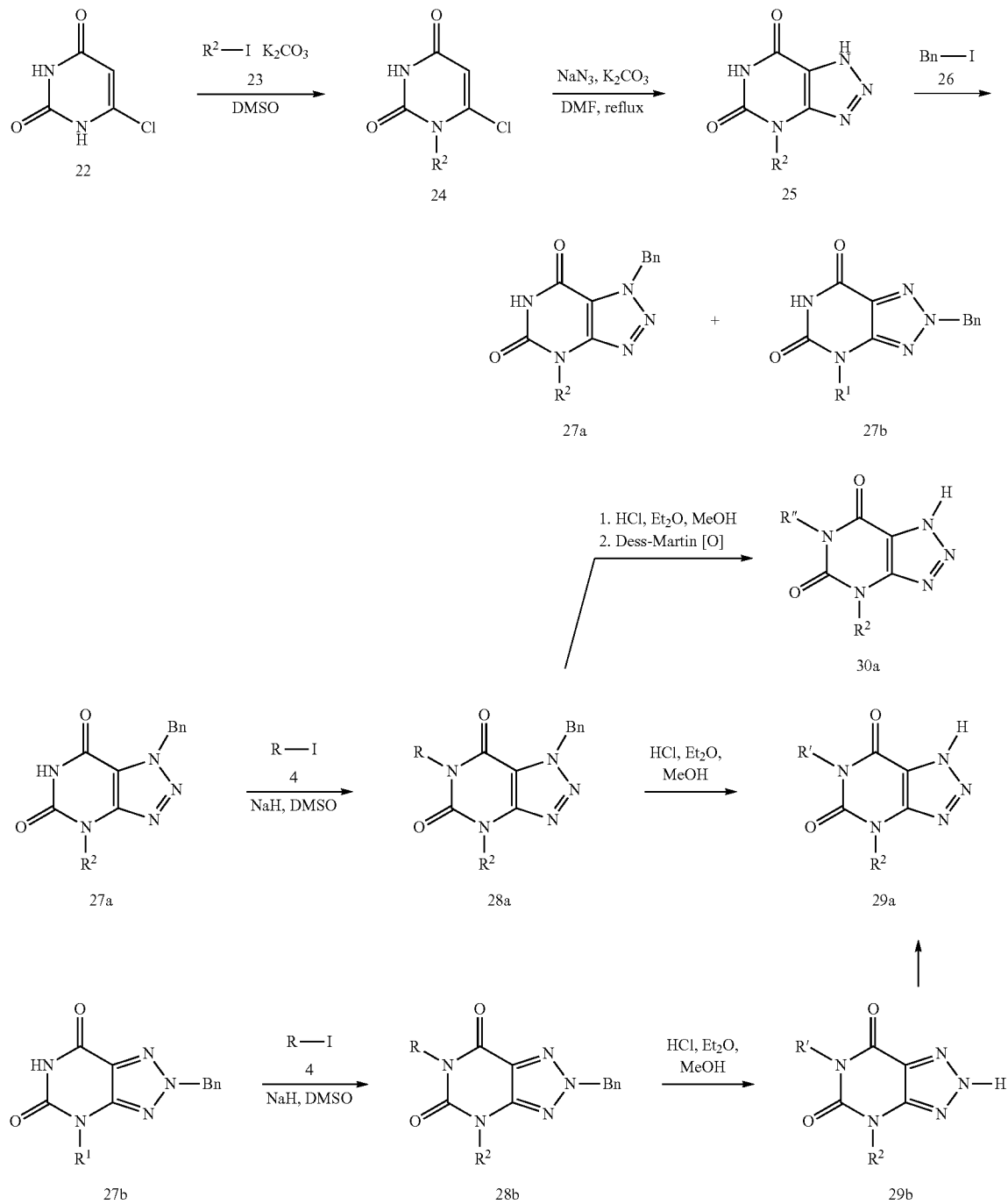

Scheme III shows an example of a synthesis of a compound of Formula B(i) wherein $Z^2$ is D and $R^7$ is hydrogen. As shown in Scheme III, 6-chloropyrimidine-2,4(1H,3H)-dione 22 is alkylated with alkyl iodide $R^2$—I 23 to give 24 in a manner analogous to that described by Pfleiderer et al., J. Heterocyclic Chem. 1998, 35, 949-54. 24 is then reacted with sodium azide and potassium carbonate analogously to what is described by Nagamatsu et al., Synthesis 2006, 4167-79 to form 1H-[1,2,3]triazolo[4,5-d]pyrimidine-5,7(4H,6H)-dione 25. 25 is treated with benzyl iodide 26 to provide a mixture of 27(a) and 27(b). 27(a) and 27(b) are then separated and each is N-alkylated with 4 analogously to what is described in U.S. Pat. No. 6,878,715 to provide, respectively, 28(a) and 28(b).

Each of 28(a) and 28(b) is then treated with HCl in methanol and ether to provide 29(a) and 29(b), respectively. 29(b) then tautomerizes to 29(a).

Alternatively, each of 28(a) and 28(b) is treated with ethereal HCl in methanol followed by subsequent Dess-Martin oxidation of 29(a) to provide 30(a).

Scheme IV. Synthesis of (A) compounds of Formula B(i) wherein $R^7 = R^1 = CH_3$ or $CD_3$ and $Z^2$ is D and (B) compounds of Formula B(ii) wherein $Z^2$ is D.

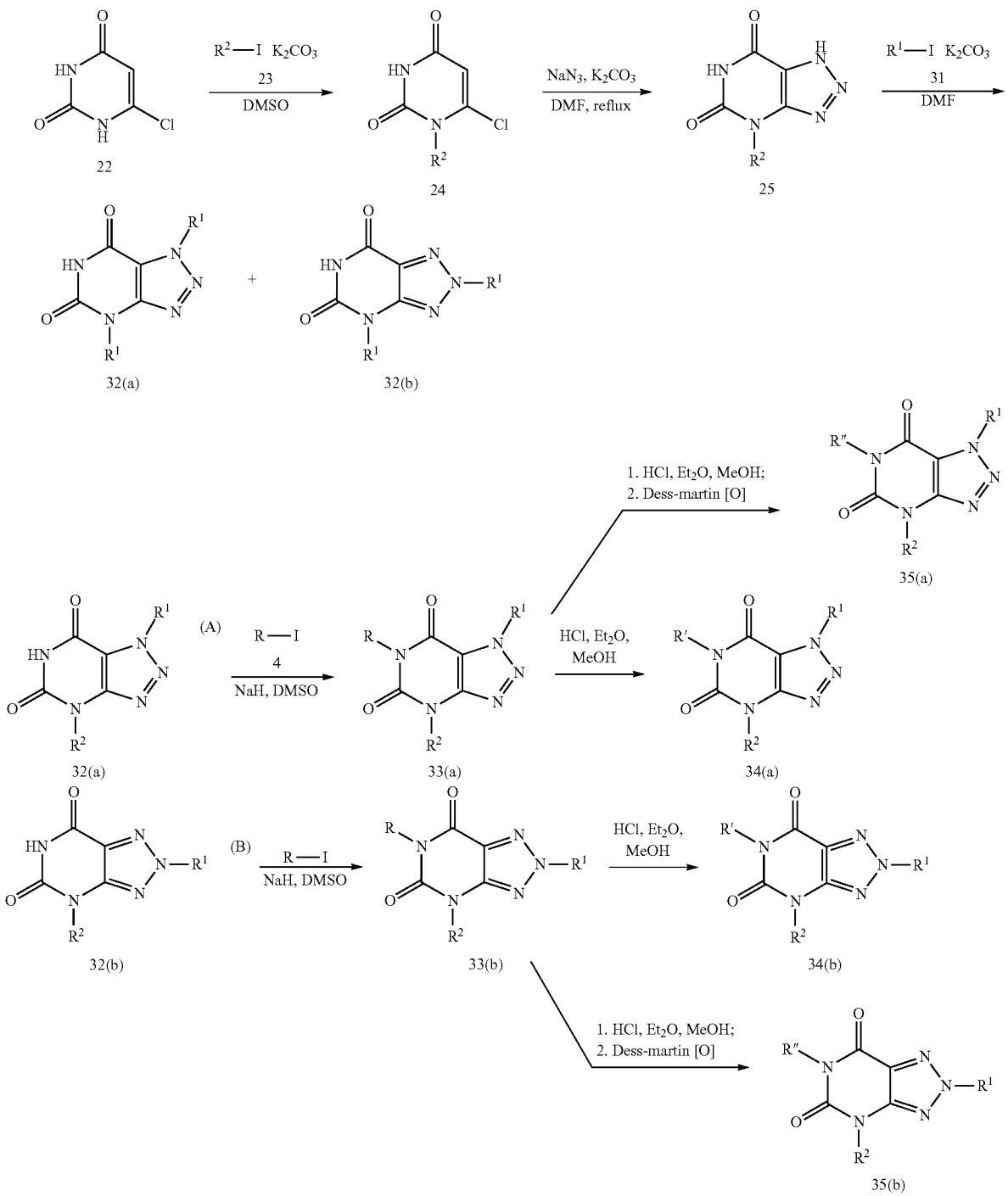

Scheme IV shows an example of a synthesis of (A) compounds of Formula B(i) wherein $Z^2$ is D and $R^7$ is $CH_3$ or $CD_3$ and (B) compounds of Formula B(ii) wherein $Z^2$ is D.

As shown in Scheme IV, 6-chloropyrimidine-2,4(1H,3H)-dione 22 is alkylated with alkyl iodide $R^2$—I 23 to give 24 in a manner analogous to that described by Pfleiderer et al., J. Heterocyclic Chem. 1998, 35, 949-54. 24 is then reacted with sodium azide and a base such as potassium carbonate analogously to what is described by Nagamatsu et al., Synthesis 2006, 4167-79 to form 1H-[1,2,3]triazolo[4,5-d]pyrimidine-5,7(4H,6H)-dione 25. 25 is treated with alkyl iodide $R^1$—I 31 in a manner analogous to Nagamatsu et al. to provide a mixture of 32(a) and 32(b). 32(a) and 32(b) are then separated.

To provide a compound of Formula B(i) (path (A)), 32(a) is N-alkylated with 4 analogously to what is described in U.S. Pat. No. 6,878,715 to provide 33(a). 33(a) is then treated with either HCl in methanol and ether to provide 34(a) or with ethereal HCl in methanol followed by subsequent Dess-Martin oxidation to provide 35(a). Both of the above alternative steps are conducted in a manner analogous to what is described in Cui et al., Biorg. Med. Chem. Lett. 2006, 16, 3401-05.

To provide a compound of Formula B(ii) (path (B)), 32(b) is N-alkylated with 4 analogously to what is described in U.S. Pat. No. 6,878,715 to provide 33(b). 33(b) is then treated with either HCl in methanol and ether to provide 34(b) or with ethereal HCl in methanol followed by subsequent Dess-Martin oxidation to provide 35(b).

Scheme V shows an example of a synthesis of a compound of Formula B(iii) wherein $Z^2$ is D. Commercially available trideuteromethylurea 1 is condensed with ethyl cyanoacetate 2 analogously to what is described by Elzein et al., J. Med. Chem. 2008, 51, 2269-78 to provide pyrimidinedione 3. Treatment of the pyrimidinedione with sodium nitrite followed by reduction with sodium dithionite is performed in a manner analogous to that described in U.S. Pat. No. 6,878,715 to provide the diamine 17, which is cyclized with thionyl chloride to form 18. N-alkylation with 4, analogously to what is described in U.S. Pat. No. 6,878,715, provides 19. 19 is then treated with either HCl in methanol and ether to provide 20 or with ethereal HCl in methanol followed by subsequent Dess-Martin oxidation to provide 21. Both of the above alternative steps are conducted in a manner analogous to what is described in Cui et al., Biorg. Med. Chem. Lett. 2006, 16, 3401-05.

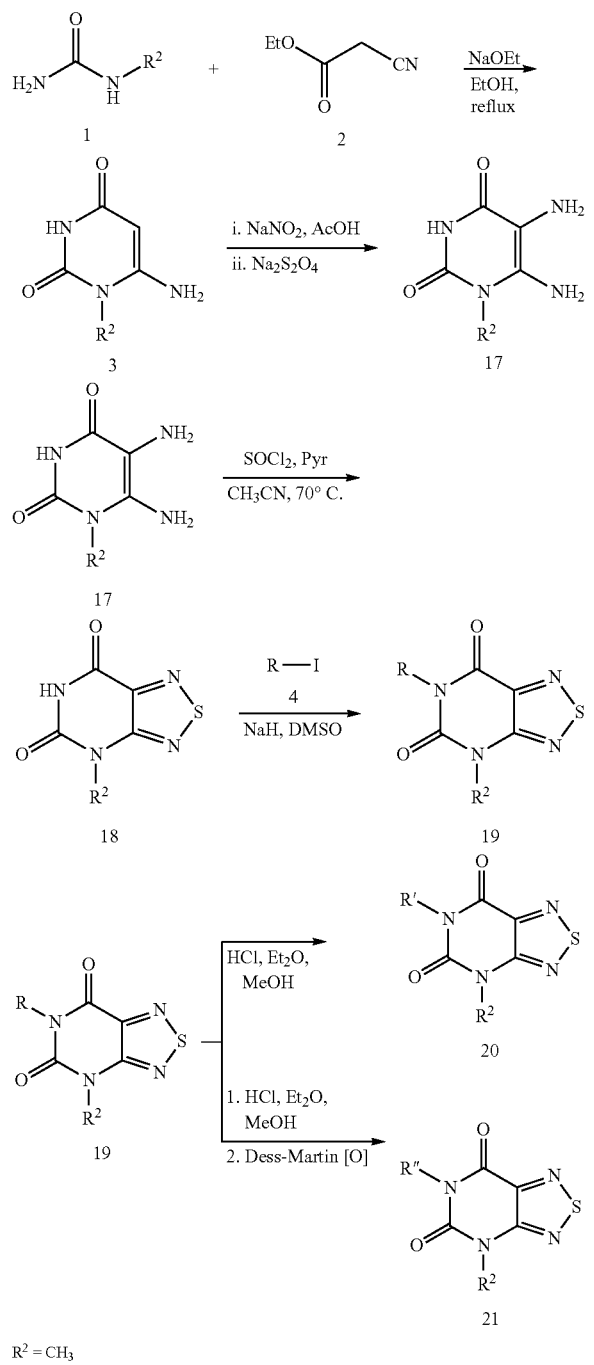

Scheme V. Synthesis of compounds of Formula B(iii) wherein $Z^2$ is D.

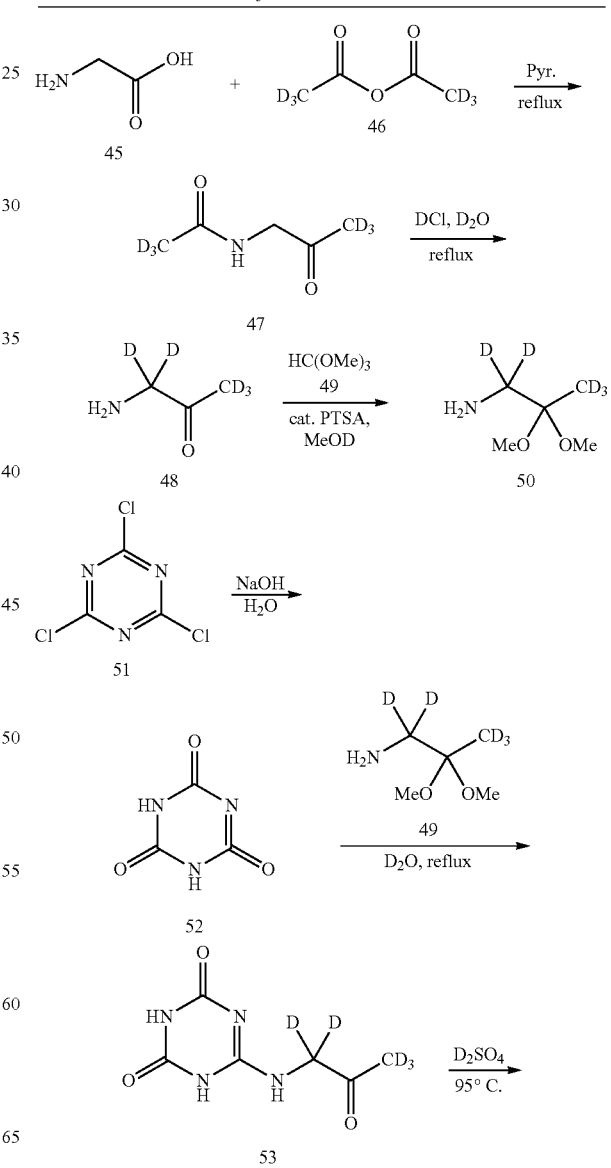

Scheme VI. Synthesis of compounds of Formula C wherein $Z^2$ is D, $R^{1a}$ is $CD_3$ and $R^5$ is deuterium

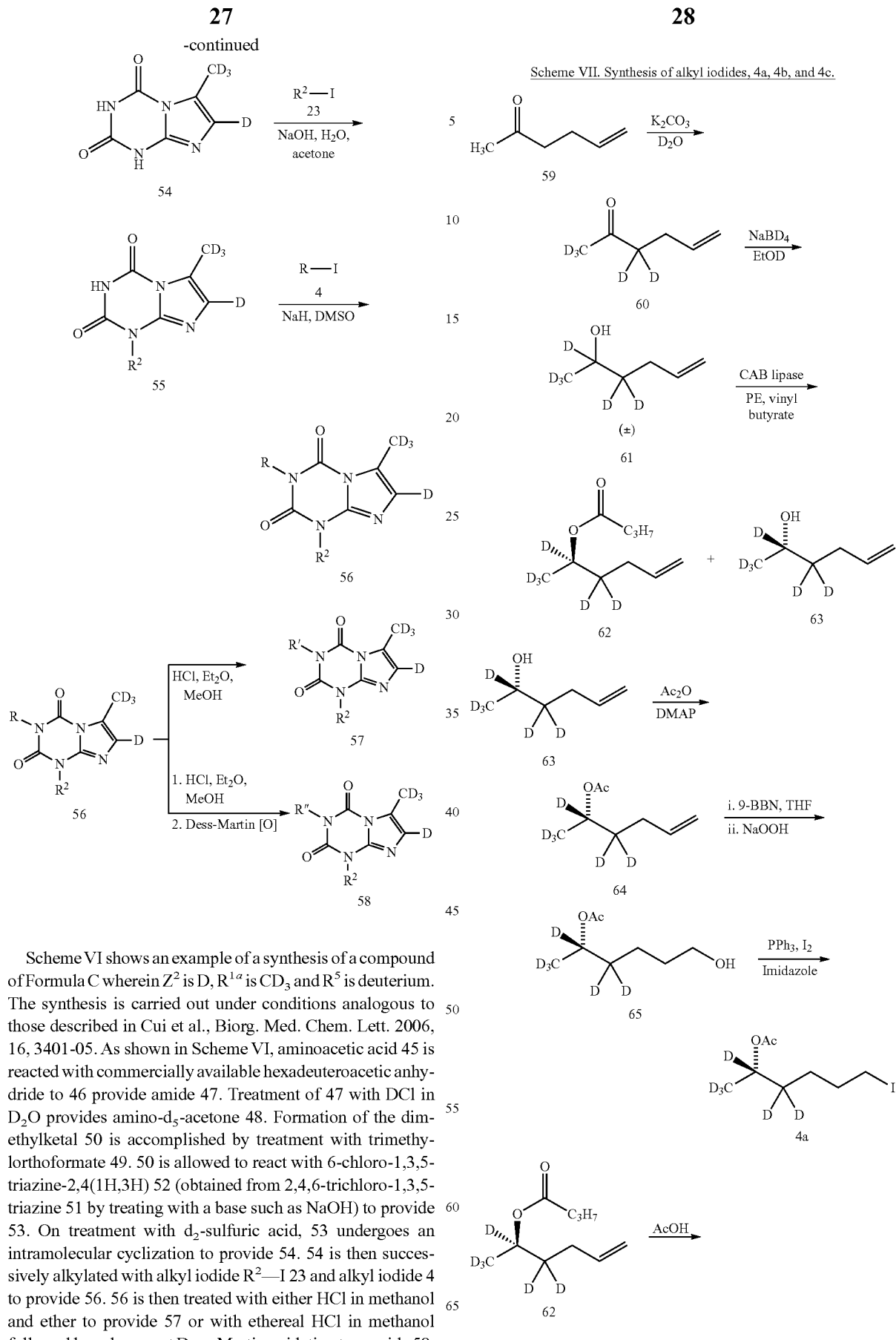

Scheme VI shows an example of a synthesis of a compound of Formula C wherein $Z^2$ is D, $R^{1a}$ is $CD_3$ and $R^5$ is deuterium. The synthesis is carried out under conditions analogous to those described in Cui et al., Biorg. Med. Chem. Lett. 2006, 16, 3401-05. As shown in Scheme VI, aminoacetic acid 45 is reacted with commercially available hexadeuteroacetic anhydride to 46 provide amide 47. Treatment of 47 with DCl in $D_2O$ provides amino-$d_5$-acetone 48. Formation of the dimethylketal 50 is accomplished by treatment with trimethylorthoformate 49. 50 is allowed to react with 6-chloro-1,3,5-triazine-2,4(1H,3H) 52 (obtained from 2,4,6-trichloro-1,3,5-triazine 51 by treating with a base such as NaOH) to provide 53. On treatment with $d_2$-sulfuric acid, 53 undergoes an intramolecular cyclization to provide 54. 54 is then successively alkylated with alkyl iodide $R^2$—I 23 and alkyl iodide 4 to provide 56. 56 is then treated with either HCl in methanol and ether to provide 57 or with ethereal HCl in methanol followed by subsequent Dess-Martin oxidation to provide 58.

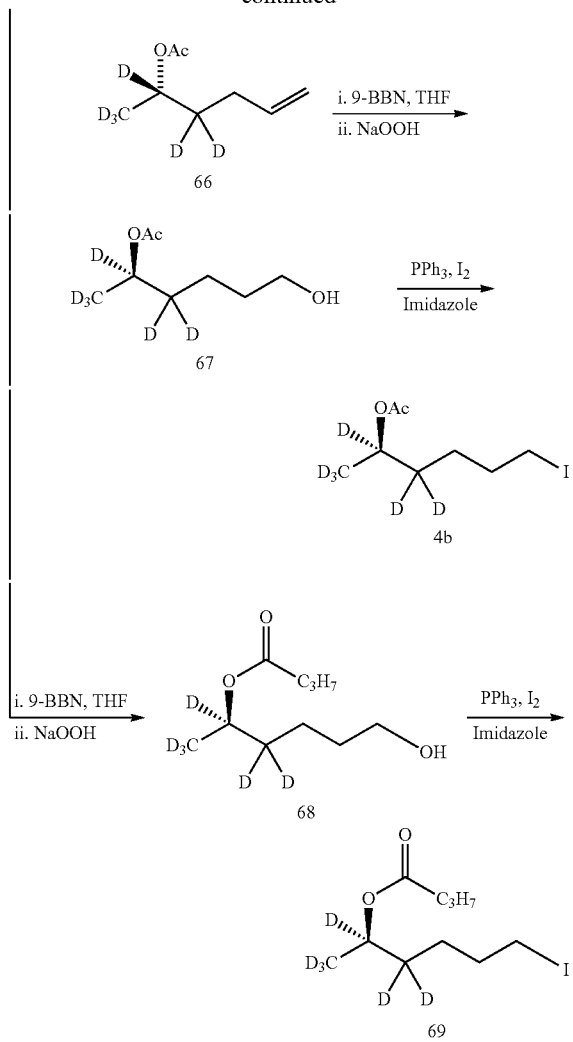

Scheme VII shows an example of a synthesis of R—I alkyl iodide 4a, 4b and 4c. To prepare 4a, the (S) enantiomer, allyl-acetone 59 is treated with base in $D_2O$ to provide the deuterated 60, which is reduced with $NaBD_4$ to provide racemic 61. Treatment of 61 in a manner analogous to that described by Conti et al. *Tetrahedron Asymm* 1998, 9, 657 affords butyric ester 62 having the (R) configuration at the carbon alpha to the $CD_3$ group and alcohol 63 having the (S) configuration at the carbon alpha to the $CD_3$ group. Acetylation of 63 followed by oxidative hydroboration of the olefinic bond and iodination of the resulting alcohol 65 provides 4a.

In a similar manner, racemic mixture 4c may be obtained from acetylation of 61 followed by oxidative hydroboration of the olefinic bond and iodination of the resulting racemic alcohol.

4b, the (R) enantiomer, may be obtained from 62 by transesterification to provide 66. Oxidative hydroboration of the olefinic bond of 66 and iodination of the resulting alcohol 67 provides 4b. Alternatively, 62 itself may undergo oxidative hydroboration of the olefinic bond, and iodination of the resulting alcohol 68 provides 69. 69 may be used instead of 4b in Schemes I-VI.

Compounds having a hydrogen in place of deuterium at the stereocenter of 61-69 and 4a-4-c shown in Scheme VII may be obtained by reacting 60 with $NaBH_4$ instead of $NaBD_4$.

Additional methods of synthesizing compounds of this invention and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, $3^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of this invention or pharmaceutically acceptable salts thereof; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz, JD and Zaffaroni, AC, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as pentoxifylline. Such agents include those indicated as being useful in combination with pentoxifylline, including but not limited to, those described in WO 1997019686, EP 0640342, WO 2003013568, WO 2001032156, WO 2006035418, and WO 1996005838.

Preferably, the second therapeutic agent is an agent useful in the treatment or prevention of a disease or condition selected from peripheral obstructive vascular disease; glomerulonephritis; nephrotic syndrome; nonalcoholic steatohepatitis; Leishmaniasis; cirrhosis; liver failure; Duchenne's muscular dystrophy; late radiation induced injuries; radiation induced lymphedema; radiation-associated necrosis; alcoholic hepatitis; radiation-associated fibrosis; necrotizing enterocolitis in premature neonates; diabetic nephropathy, hypertension-induced renal failure, and other chronic kidney disease; Focal Segmental Glomerulosclerosis; pulmonary sarcoidosis; recurrent aphthous stomatitis; chronic breast pain in breast cancer patients; brain and central nervous system tumors; malnutrition-inflammation-cachexia syndrome; interleukin-1 mediated disease; graft versus host reaction and other allograft reactions; diet-induced fatty liver conditions, atheromatous lesions, fatty liver degeneration and other diet-induced high fat or alcohol-induced tissue-degenerative conditions; human immunodeficiency virus type 1 (HIV-1) and other human retroviral infections; multiple sclerosis; cancer; fibroproliferative diseases; fungal infection; drug-induced nephrotoxicity; collagenous colitis and other diseases and/or conditions characterized by elevated levels of platelet derived growth factor (PDGF) or other inflammatory cytokines; endometriosis; optic neuropathy and CNS impairments associated with acquired immunodeficiency syndrome (AIDS), immune disorder diseases, or multiple sclerosis; autoimmune disease; upper respiratory viral infection; depression; urinary incontinence; irritable bowel syndrome; septic shock; Alzheimers Dementia; neuropathic pain; dysuria; retinal or optic nerve damage; peptic ulcer; insulin-dependent diabetes; non-insulin-dependent diabetes; diabetic nephropathy; metabolic syndrome; obesity; insulin resistance; dyslipidemia; pathological glucose tolerance; hypertension; hyperlipidemia; hyperuricemia; gout; hypercoagulability; and inflammation or injury associated with neutrophil chemotaxis and/or degranulation. The compounds of this invention can also be used to control intraocular pressure or to stabilize auto-regulation of cerebral blood flow in subjects who require such control as determined by medical examination.

In one embodiment, the second therapeutic agent is selected from α-tocopherol and hydroxyurea.

In another embodiment, the second therapeutic agent is useful in the treatment of diabetes or an associated disorder, and is selected from insulin or insulin analogues, glucagon-like-peptide-1 (GLP-1) receptor agonists, sulfonylurea agents, biguanide agents, alpha-glucosidase inhibitors, PPAR agonists, meglitinide agents, dipeptidyl-peptidase (DPP) IV inhibitors, other phosphodiesterase (PDE1, PDE5, PDE9, PDE10 or PDE1) inhibitors, amylin agonists, CoEnzyme A inhibitors, and antiobesity agents.

Specific examples of insulin include, but are not limited to Humulin® (human insulin, rDNA origin), Novolin® (human insulin, rDNA origin), Velosulin® BR (human buffered regular insulin, rDNA origin), Exubera® (human insulin, inhaled), and other forms of inhaled insulin, for instance, as delivered by Mannkind's "Technosphere Insulin System".

Specific examples of insulin analogues include, but are not limited to, novarapid, insulin detemir, insulin lispro, insulin glargine, insulin zinc suspension and Lys-Pro insulin.

Specific examples of Glucagon-Like-Peptide-1 receptor agonists include, but are not limited to BIM-51077 (CAS-No. 275371-94-3), EXENATIDE (CAS-No. 141758-74-9), CJC-1131 (CAS-No. 532951-64-7), LIRAGLUTIDE (CAS-No. 20656-20-2) and ZP-10 (CAS-No. 320367-13-3).

Specific examples of sulfonylurea agents include, but are not limited to, TOLBUTAMIDE (CAS-No. 000064-77-7), TOLAZAMIDE (CAS-No. 001156-19-0), GLIPIZIDE (CAS-No. 029094-61-9), CARBUTAMIDE (CAS-No. 000339-43-5), GLISOXEPIDE (CAS-No. 025046-79-1), GLISENTIDE (CAS-No. 032797-92-5), GLIBORNURIDE (CAS-No. 026944-48-9), GLIBENCLAMIDE (CAS-NO. 010238-21-8), GLIQUIDONE (CAS-No. 033342-05-1), GLIMEPIRIDE (CAS-No. 093479-97-1) and GLICLAZIDE (CAS-No. 021187-98-4).

A specific example of a biguanide agent includes, but is not limited to METFORMIN(CAS-No. 000657-24-9).

Specific examples of alpha-glucosidase-inhibitors include, but are not limited to ACARBOSE (Cas-No. 056180-94-0), MIGLITOL (CAS-No. 072432-03-2) and VOGLIBOSE (CAS-No. 083480-29-9).

Specific examples of PPAR-agonists include, but are not limited to MURAGLITAZAR (CAS-No. 331741-94-7), ROSIGLITAZONE (CAS-NO. 122320-73-4), PIOGLITAZONE (CAS-No. 111025-46-8), RAGAGLITAZAR (CAS-NO. 222834-30-2), FARGLITAZAR (CAS-No. 196808-45-4), TESAGLITAZAR (CAS-No. 251565-85-2), NAVEGLITAZAR (CAS-No. 476436-68-7), NETOGLITAZONE (CAS-NO. 161600-01-7), RIVOGLITAZONE (CAS-NO. 185428-18-6), K-1 11 (CAS-No. 221564-97-2), GW-677954 (CAS-No. 622402-24-8), FK-614 (CAS-No 193012-35-0) and (−)-Halofenate (CAS-No. 024136-23-0). Preferred PPAR-agonists are ROSGLITAZONE and PIOGLITAZONE.

Specific examples of meglitinide agents include, but are not limited to REPAGLINIDE (CAS-No. 135062-02-1), NATEGLINIDE (CAS-No. 105816-04-4) and MITIGLINIDE (CAS-No. 145375-43-5).

Specific examples of DPP IV inhibitors include, but are not limited to SITAGLIPTIN(CAS-No. 486460-32-6), SAXAGLIPTIN(CAS-No. 361442-04-8), VILDAGLIPTIN(CAS-No. 274901-16-5), DENAGLIPTIN(CAS-No. 483369-58-0), P32/98 (CAS-No. 251572-70-0) and NVP-DPP-728 (CAS-No. 247016-69-9).

Specific examples of PDE5 inhibitors include, but are not limited to SILDENAFIL (CAS-No. 139755-83-2), VARDENAFIL (CAS-No. 224785-90-4) and TADALAFIL (CAS-No. 171596-29-5). Examples of PDE1, PDE9, PDE10 or PDE11 inhibitors which may be usefully employed according to the present invention can be found, for example, in US20020160939, WO2003037432, US2004220186, WO2005/003129, WO2005012485, WO2005120514 and WO03077949.

A specific example of an amylin agonist includes, but is not limited to PRAMLINITIDE (CAS-No. 151126-32-8).

A specific example of a Coenzyme A inhibitor includes, but is not limited to ETOMOXIR (CAS-No. 082258-36-4).

Specific examples of anti-obesity drugs include, but are not limited to HMR-1426 (CAS-No. 262376-75-0), CETILISTAT (CAS-No. 282526-98-1) and SIBUTRAMINE (CAS-No. 106650-56-0).

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be determined approximately from height and weight of the patient. See, e.g., Scientific Tables, Geigy Pharmaceuticals, Ardsley, N.Y., 1970, 537.

In one embodiment, an effective amount of a compound of this invention is in the range of 20 mg to 2000 mg per treatment. In more specific embodiments the amount is in the range of 40 mg to 1000 mg, or in the range of 100 mg to 800 mg, or more specifically in the range of 200 mg to 400 mg per treatment. Treatment typically is administered from one to three times daily.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for pentoxifylline.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In one embodiment, the invention provides a method of inhibiting the activity of phosphodiesterase (PDE) in a cell, comprising contacting a cell with one or more compounds of Formula A, B, or C.

In addition to its PDE inhibitory activity, pentoxifylline is known to suppress the production of a number of other biological agents such as interleukin-1 (IL-1), IL-6, IL-12, TNF-alpha, fibrinogen, and various growth factors. Accordingly, in another embodiment, the invention provides a method of suppressing the production of interleukin-1 (IL-1), IL-6, IL-12, TNF-alpha, fibrinogen, and various growth factors in a cell, comprising contacting a cell with one or more compounds of Formula A, B, or C.

According to another embodiment, the invention provides a method of treating a disease in a patient in need thereof that is beneficially treated by pentoxifylline comprising the step of administering to said patient an effective amount of a compound of Formula A, B, or C or pharmaceutically acceptable salt thereof or a pharmaceutical composition comprising a compound of Formula A, B, or C and a pharmaceutically acceptable carrier.

Such diseases are well known in the art and are disclosed in, but not limited to the following patents and published applications: WO 1988004928, EP 0493682, U.S. Pat. No. 5,112,827, EP 0484785, WO 1997019686, WO 2003013568, WO 2001032156, WO 1992007566, WO 1998055110, WO 2005023193, U.S. Pat. No. 4,975,432, WO 1993018770, EP 0490181, and WO 1996005836. Such diseases include, but are not limited to, peripheral obstructive vascular disease; glomerulonephritis; nephrotic syndrome; nonalcoholic steatohepatitis; Leishmaniasis; cirrhosis; liver failure; Duchenne's muscular dystrophy; late radiation induced injuries; radiation induced lymphedema; radiation-associated necrosis; alcoholic hepatitis; radiation-associated fibrosis; necrotizing enterocolitis in premature neonates; diabetic nephropathy, hypertension-induced renal failure, and other chronic kidney disease; Focal Segmental Glomerulosclerosis; pulmonary sarcoidosis; recurrent aphthous stomatitis; chronic breast pain in breast cancer patients; brain and central nervous system tumors; malnutrition-inflammation-cachexia syndrome; interleukin-1 mediated disease; graft versus host reaction and other allograft reactions; diet-induced fatty liver conditions, atheromatous lesions, fatty liver degeneration and other diet-induced high fat or alcohol-induced tissue-degenerative conditions; human immunodeficiency virus type 1 (HIV-1) and other human retroviral infections; multiple sclerosis; cancer; fibroproliferative diseases; fungal infection; drug-induced nephrotoxicity; collagenous colitis and other diseases and/or conditions characterized by elevated levels of platelet derived growth factor (PDGF) or other inflammatory cytokines; endometriosis; optic neuropathy and CNS impairments associated with acquired immunodeficiency syndrome (AIDS), immune disorder diseases, or multiple sclerosis; autoimmune disease; upper respiratory viral infection; depression; urinary incontinence; irritable bowel syndrome; septic shock; Alzheimers Dementia; neuropathic pain; dysuria; retinal or optic nerve damage; peptic ulcer; insulin-dependent diabetes; non-insulin-dependent diabetes; diabetic nephropathy; metabolic syndrome; obesity; insulin resistance; dyslipidemia; pathological glucose tolerance; hypertension; hyperlipidemia; hyperuricemia; gout; hypercoagulability; acute alcoholic hepatitis; olfaction disorders; patent ductus arteriosus; and inflammation or injury associated with neutrophil chemotaxis and/or degranulation.

The compounds are also useful for treating IL-12 or Th1 mediated diseases, including inflammatory diseases or disorders, such as, for example, arthritis, asthma, psoriasis, and adult respiratory distress syndrome; autoimmune diseases or disorders, such as, for example, autoimmune gastritis, autoimmune neutropenia, chronic active hepatitis, chronic thyroiditis, Crohn's Disease, ulcerative colitis, systemic lupus erythematosus, myasthenia gravis, rheumatoid arthritis, scleroderma, thrombocytopenia, thyroid diseases (e.g., Graves' and Hashimoto's disease), type-1-IDDM, and uveitis; and neurodegenerative diseases such as, for example, amyotrophic lateral sclerosis, Parkinson's disease, and primary lateral sclerosis.

The compounds of Formula A, B, or C can also be used to control intraocular pressure or to stabilize auto-regulation of cerebral blood flow in subjects who require such control as determined by medical examination.

In one particular embodiment, the method of this invention is used to treat a disease or condition in a patient in need thereof selected from intermittent claudication on the basis of chronic occlusive arterial disease of the limbs and other peripheral obstructive vascular diseases; glomerulonephritis; Focal Segmental Glomerulosclerosis; nephrotic syndrome; nonalcoholic steatohepatitis; Leishmaniasis; cirrhosis; liver failure; Duchenne's muscular dystrophy; late radiation induced injuries; radiation induced lymphedema; alcoholic hepatitis; radiation-induced fibrosis; necrotizing enterocolitis in premature neonates; diabetic nephropathy, hypertension-induced renal failure and other chronic kidney diseases; pulmonary sarcoidosis; recurrent aphthous stomatitis; chronic breast pain in breast cancer patients; brain and central nervous system tumors; obesity; acute alcoholic hepatitis; olfaction disorders; endometriosis-associated infertility; malnutrition-inflammation-cachexia syndrome; and patent ductus arteriosus.

In one embodiment, the method of this invention is used to treat diabetic nephropathy, hypertensive nephropathy or intermittent claudication on the basis of chronic occlusive arterial disease of the limbs. In another particular embodiment, the method of this invention is used to treat a disease or condition in a patient in need thereof selected from intermittent claudication on the basis of chronic occlusive arterial disease of the limbs.

In one embodiment, the method of this invention is used to treat chronic kidney disease. The chronic kidney disease may be selected from glomerulonephritis, focal segmental glomerulosclerosis, nephrotic syndrome, reflux uropathy, or polycystic kidney disease.

In one embodiment, the method of this invention is used to treat chronic disease of the liver. The chronic disease of the liver may be selected from nonalcoholic steatohepatitis, fatty liver degeneration or other diet-induced high fat or alcohol-induced tissue-degenerative conditions, cirrhosis, liver failure, or alcoholic hepatitis.

In one embodiment, the method of this invention is used to a diabetes-related disease or condition. This disease may be selected from insulin resistance, retinopathy, diabetic ulcers, radiation-associated necrosis, acute kidney failure or drug-induced nephrotoxicity.

In one embodiment, the method of this invention is used to treat a patient suffering from cystic fibrosis, including those patients suffering from chronic Pseudomonas bronchitis.

In one embodiment, the method of this invention is used to aid in wound healing. Examples of types of wounds that may be treated include venous ulcers, diabetic ulcers and pressure ulcers.

In another particular embodiment, the method of this invention is used to treat a disease or condition in a patient in need thereof selected from insulin dependent diabetes; non-insulin dependent diabetes; metabolic syndrome; obesity; insulin resistance; dyslipidemia; pathological glucose tolerance; hypertension; hyperlipidemia; hyperuricemia; gout; and hypercoagulability.

In one embodiment, the method of this invention is used to treat a disease or condition in a patient in need thereof wherein the disease or condition is selected from anemia, Graves disease, retinal vein occlusion, lupus nephritis, macular degeneration, myelodysplasia, pruritus of HIV origin, pulmonary hypertension, retinal artery occlusion, intestinal inflammation, ischemic optic neuropathy, acute pancreatitis, sickle cell anemia and beta thalassemia.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to the patient one or more second therapeutic agents. The choice of second therapeutic agent may be made from any second therapeutic agent known to be useful for co-administration with pentoxifylline. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula A, B, or C and a second therapeutic agent for treatment of the following conditions (with the particular second therapeutic agent indicated in parentheses following the indication): late radiation induced injuries α-tocopherol), radiation-induced fibrosis (α-tocopherol), radiation induced lymphedema (α-tocopherol), chronic breast pain in breast cancer patients (α-tocopherol), type 2 diabetic nephropathy (captopril), malnutrition-inflammation-cachexia syndrome (oral nutritional supplement, such as Nepro; and oral anti-inflammatory module, such as Oxepa); and brain and central nervous system tumors (radiation therapy and hydroxyurea).

The combination therapies of this invention also include co-administering a compound of Formula A, B, or C and a second therapeutic agent for treatment of insulin dependent diabetes; non-insulin dependent diabetes; metabolic syndrome; obesity; insulin resistance; dyslipidemia; pathological glucose tolerance; hypertension; hyperlipidemia; hyperuricemia; gout; and hypercoagulability.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula A, B, or C alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula A, B, or C for use in the treatment or prevention in a patient of a disease, disorder or symptom thereof delineated herein.

Diagnostic Methods and Kits

The present invention also provides kits for use to treat peripheral obstructive vascular disease, in particular intermittent claudication on the basis of chronic occlusive arterial disease of the limbs; glomerulonephritis; nephrotic syndrome; nonalcoholic steatohepatitis; Leishmaniasis; cirrhosis; liver failure; Duchenne's muscular dystrophy; late radiation induced injuries; radiation induced lymphedema; alcoholic hepatitis; radiation fibrosis; necrotizing enterocolitis in premature neonates; chronic kidney disease; pulmonary sarcoidosis; recurrent aphthous stomatitis; chronic breast pain in breast cancer patients; brain and central nervous system tumors; malnutrition-inflammation-cachexia syndrome; insulin dependent diabetes; non-insulin dependent diabetes; metabolic syndrome; obesity; insulin resistance; dyslipidemia; pathological glucose tolerance; hypertension; hyperlipidemia; hyperuricemia; gout; and hypercoagulability. These kits comprise (a) a pharmaceutical composition comprising a compound of Formula A, B, or C or a salt thereof, wherein said pharmaceutical composition is in a container; and (b) instructions describing a method of using the pharmaceutical composition to treat peripheral obstructive vascular disease, in particular intermittent claudication on the basis of chronic occlusive arterial disease of the limbs; glomerulonephritis; nephrotic syndrome; nonalcoholic steatohepatitis; Leishmaniasis; cirrhosis; liver failure; Duchenne's muscular dystrophy; late radiation induced injuries; radiation induced lymphedema; alcoholic hepatitis; radiation fibrosis; necrotizing enterocolitis in premature neonates; chronic kidney disease; pulmonary sarcoidosis; recurrent aphthous stomatitis; chronic breast pain in breast cancer patients; brain and central nervous system tumors; malnutrition-inflammation-cachexia syndrome; insulin dependent diabetes; non-insulin dependent diabetes; metabolic syndrome; obesity; insulin resistance; dyslipidemia; pathological glucose tolerance; hypertension; hyperlipidemia; hyperuricemia; gout; and hypercoagulability.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

Biological Evaluation

EXAMPLES

Example 1

Evaluation of Metabolic Stability in Human Liver Microsomes

Human liver microsomes (20 mg/mL) are available from Xenotech, LLC (Lenexa, Kans.). β-nicotinamide adenine dinucleotide phosphate, reduced form (NADPH), magnesium chloride (MgCl$_2$), and dimethyl sulfoxide (DMSO) are available from Sigma-Aldrich.

7.5 mM stock solutions of test compounds are prepared in DMSO. The 7.5 mM stock solutions are diluted to 12.5-50 μM in acetonitrile (ACN). The 20 mg/mL human liver microsomes are diluted to 0.625 mg/mL in 0.1 M potassium phosphate buffer, pH 7.4, containing 3 mM MgCl$_2$. The diluted microsomes are added to wells of a 96-well deep-well polypropylene plate in triplicate. A 10 μL aliquot of the 12.5-50 μM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 μM test compound, and 2 mM NADPH in 0.1 M potassium phosphate buffer, pH 7.4, and 3 mM MgCl$_2$. The reaction mixtures are incubated at 37° C., and 50 μL aliquots are removed at 0, 5, 10, 20, and 30 minutes and added to shallow-well 96-well plates which contain 50 μL of ice-cold ACN with internal standard to stop the reactions. The plates are stored at 4° C. for 20 minutes after which 100 μL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for NS-304, MRE-269 and the positive control, 7-ethoxycoumarin (1 μM). Testing is done in triplicate.

The in vitro $t_{1/2}$s for test compounds are calculated from the slopes of the linear regression of % parent remaining (ln) vs incubation time relationship:

in vitro $t_{1/2}$=0.693/$k$ k=−[slope of linear regression of % parent remaining (ln) vs incubation time]. Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:
1. A compound of Formula A:

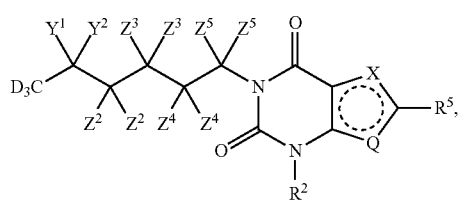

or a pharmaceutically acceptable salt thereof, wherein
each $Z^2$ is hydrogen or deuterium;
each $Z^3$ is hydrogen or deuterium;
each $Z^4$ is hydrogen or deuterium;
each $Z^5$ is hydrogen or deuterium;

the bicyclic ring system bearing X and Q is:
a 1H-pyrrolo[2,3-d]pyrimidine-2,4(3H,7H)-dione ring where X is CR$^{1a}$ and Q is NR$^7$;
either (a) $Y^1$ is OH, and $Y^2$ is hydrogen or deuterium, or (b) $Y^1$ and $Y^2$ are taken together with the carbon to which they are attached to form C=O;
R$^{1a}$ is hydrogen, —CH$_3$ or —CD$_3$;
R$^2$ is —CH$_3$ or —CD$_3$;
R$^5$ is hydrogen or deuterium; and
R$^7$ is —CH$_3$, —CD$_3$, hydrogen or deuterium; and wherein any atom not designated as deuterium is present at its natural isotopic abundance.

2. The compound of claim 1, wherein the compound has the Formula A(i) wherein the bicyclic ring system bearing X and Q is a 1H-pyrrolo[2,3-d]pyrimidine-2,4(3H,7H)-dione ring:

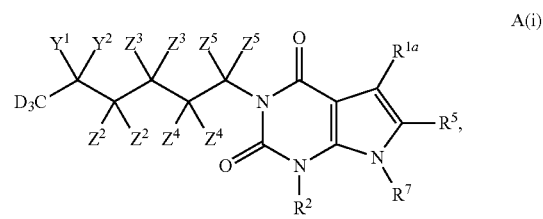

or a pharmaceutically acceptable salt thereof.

3. The compound of claim 2, wherein R$^{1a}$ is CH$_3$.
4. The compound of claim 2, wherein R$^{1a}$ is CD$_3$.
5. The compound of claim 2, wherein R$^{1a}$ is hydrogen.
6. The compound of claim 2, wherein R$^2$ is CH$_3$.
7. The compound of claim 2, wherein R$^2$ is CD$_3$.
8. The compound of claim 1, wherein each $Z^2$, $Z^3$, $Z^4$ and $Z^5$ is hydrogen.
9. The compound of claim 1, wherein each $Z^2$, $Z^3$, $Z^4$ and $Z^5$ is deuterium.
10. The compound of claim 1, wherein $Z^2$ is deuterium and either each of $Z^3$, $Z^4$ and $Z^5$ is hydrogen or each of $Z^3$, $Z^4$ and $Z^5$ is deuterium.
11. The compound of claim 1, wherein $Y^1$ and $Y^2$ are taken together with the carbon to which they are attached to form C=O.
12. The compound of claim 1, wherein $Y^1$ is OH, and $Y^2$ is hydrogen or deuterium.
13. The compound of claim 2, wherein the compound is of Formula A(i), wherein R$^7$ is hydrogen, $Z^3$, $Z^4$, and $Z^5$ are each hydrogen, and the compound is selected from the group consisting of the compounds in the table below:

| Compound | R$^{1a}$ | R$^2$ | R$^5$ | $Z^2$ | $Y^1$ | $Y^2$ |
| --- | --- | --- | --- | --- | --- | --- |
| 100 | CH$_3$ | CH$_3$ | H | H | taken together as =O | |
| 101 | CD$_3$ | CH$_3$ | H | H | taken together as =O | |
| 102 | CH$_3$ | CD$_3$ | H | H | taken together as =O | |
| 103 | CD$_3$ | CD$_3$ | H | H | taken together as =O | |
| 104 | CH$_3$ | CH$_3$ | H | D | taken together as =O | |
| 105 | CD$_3$ | CH$_3$ | H | D | taken together as =O | |
| 106 | CH$_3$ | CD$_3$ | H | D | taken together as =O | |
| 107 | CD$_3$ | CD$_3$ | H | D | taken together as =O | |
| 108 | CH$_3$ | CH$_3$ | D | H | taken together as =O | |
| 109 | CD$_3$ | CH$_3$ | D | H | taken together as =O | |
| 110 | CH$_3$ | CD$_3$ | D | H | taken together as =O | |
| 111 | CD$_3$ | CD$_3$ | D | H | taken together as =O | |
| 112 | CH$_3$ | CH$_3$ | D | D | taken together as =O | |
| 113 | CD$_3$ | CH$_3$ | D | D | taken together as =O | |
| 114 | CH$_3$ | CD$_3$ | D | D | taken together as =O | |
| 115 | CD$_3$ | CD$_3$ | D | D | taken together as =O | |

-continued

| Compound | R$^{1a}$ | R$^2$ | R$^5$ | Z$^2$ | Y$^1$ | Y$^2$ |
|---|---|---|---|---|---|---|
| 116 | CH$_3$ | CH$_3$ | H | H | OH | H |
| 117 | CD$_3$ | CH$_3$ | H | H | OH | H |
| 118 | CH$_3$ | CD$_3$ | H | H | OH | H |
| 119 | CD$_3$ | CD$_3$ | H | H | OH | H |
| 120 | CH$_3$ | CH$_3$ | H | D | OH | H |
| 121 | CD$_3$ | CH$_3$ | H | D | OH | H |
| 122 | CH$_3$ | CD$_3$ | H | D | OH | H |
| 123 | CD$_3$ | CD$_3$ | H | D | OH | H |
| 124 | CH$_3$ | CH$_3$ | D | H | OH | H |
| 125 | CD$_3$ | CH$_3$ | D | H | OH | H |
| 126 | CH$_3$ | CD$_3$ | D | H | OH | H |
| 127 | CD$_3$ | CD$_3$ | D | H | OH | H |
| 128 | CH$_3$ | CH$_3$ | D | D | OH | H |
| 129 | CD$_3$ | CH$_3$ | D | D | OH | H |
| 130 | CH$_3$ | CD$_3$ | D | D | OH | H |
| 131 | CD$_3$ | CD$_3$ | D | D | OH | H |
| 132 | CH$_3$ | CH$_3$ | H | H | OH | D |
| 133 | CD$_3$ | CH$_3$ | H | H | OH | D |
| 134 | CH$_3$ | CD$_3$ | H | H | OH | D |
| 135 | CD$_3$ | CD$_3$ | H | H | OH | D |
| 136 | CH$_3$ | CH$_3$ | H | D | OH | D |
| 137 | CD$_3$ | CH$_3$ | H | D | OH | D |
| 138 | CH$_3$ | CD$_3$ | H | D | OH | D |
| 139 | CD$_3$ | CD$_3$ | H | D | OH | D |
| 140 | CH$_3$ | CH$_3$ | D | H | OH | D |
| 141 | CD$_3$ | CH$_3$ | D | H | OH | D |
| 142 | CH$_3$ | CD$_3$ | D | H | OH | D |
| 143 | CD$_3$ | CD$_3$ | D | H | OH | D |
| 144 | CH$_3$ | CH$_3$ | D | D | OH | D |
| 145 | CD$_3$ | CH$_3$ | D | D | OH | D |
| 146 | CH$_3$ | CD$_3$ | D | D | OH | D |
| 147 | CD$_3$ | CD$_3$ | D | D | OH | D | or a pharmaceutically acceptable salt of the compound.

14. The compound of claim 2, wherein the compound is of Formula A(i), wherein R$^7$ is CH$_3$ or CD$_3$, Z$^3$, Z$^4$, and Z$^5$ are each hydrogen, and the compound is selected from the group consisting of the compounds in the table below:

| Compound | R$^7$ | R$^{1a}$ | R$^2$ | R$^5$ | Z$^2$ | Y$^1$ | Y$^2$ |
|---|---|---|---|---|---|---|---|
| 200 | CH$_3$ | H | CH$_3$ | H | H | taken together as =O | |
| 201 | CD$_3$ | H | CH$_3$ | H | H | taken together as =O | |
| 202 | CH$_3$ | H | CD$_3$ | H | H | taken together as =O | |
| 203 | CD$_3$ | H | CD$_3$ | H | H | taken together as =O | |
| 204 | CH$_3$ | H | CH$_3$ | H | D | taken together as =O | |
| 205 | CD$_3$ | H | CH$_3$ | H | D | taken together as =O | |
| 206 | CH$_3$ | H | CD$_3$ | H | D | taken together as =O | |
| 207 | CD$_3$ | H | CD$_3$ | H | D | taken together as =O | |
| 208 | CH$_3$ | H | CH$_3$ | D | H | taken together as =O | |
| 209 | CD$_3$ | H | CH$_3$ | D | H | taken together as =O | |
| 210 | CH$_3$ | H | CD$_3$ | D | H | taken together as =O | |
| 211 | CD$_3$ | H | CD$_3$ | D | H | taken together as =O | |
| 212 | CH$_3$ | H | CH$_3$ | D | D | taken together as =O | |
| 213 | CD$_3$ | H | CH$_3$ | D | D | taken together as =O | |
| 214 | CH$_3$ | H | CD$_3$ | D | D | taken together as =O | |
| 215 | CD$_3$ | H | CD$_3$ | D | D | taken together as =O | |
| 216 | CH$_3$ | H | CH$_3$ | H | H | OH | H |
| 217 | CD$_3$ | H | CH$_3$ | H | H | OH | H |
| 218 | CH$_3$ | H | CD$_3$ | H | H | OH | H |
| 219 | CD$_3$ | H | CD$_3$ | H | H | OH | H |
| 220 | CH$_3$ | H | CH$_3$ | H | D | OH | H |
| 221 | CD$_3$ | H | CH$_3$ | H | D | OH | H |
| 222 | CH$_3$ | H | CD$_3$ | H | D | OH | H |
| 223 | CD$_3$ | H | CD$_3$ | H | D | OH | H |
| 224 | CH$_3$ | H | CH$_3$ | D | H | OH | H |
| 225 | CD$_3$ | H | CH$_3$ | D | H | OH | H |
| 226 | CH$_3$ | H | CD$_3$ | D | H | OH | H |
| 227 | CD$_3$ | H | CD$_3$ | D | H | OH | H |
| 228 | CH$_3$ | H | CH$_3$ | D | D | OH | H |
| 229 | CD$_3$ | H | CH$_3$ | D | D | OH | H |
| 230 | CH$_3$ | H | CD$_3$ | D | D | OH | H |
| 231 | CD$_3$ | H | CD$_3$ | D | D | OH | H |
| 232 | CH$_3$ | H | CH$_3$ | H | H | OH | D |
| 233 | CD$_3$ | H | CH$_3$ | H | H | OH | D |
| 234 | CH$_3$ | H | CD$_3$ | H | H | OH | D |
| 235 | CD$_3$ | H | CD$_3$ | H | H | OH | D |
| 236 | CH$_3$ | H | CH$_3$ | H | D | OH | D |
| 237 | CD$_3$ | H | CH$_3$ | H | D | OH | D |
| 238 | CH$_3$ | H | CD$_3$ | H | D | OH | D |
| 239 | CD$_3$ | H | CD$_3$ | H | D | OH | D |
| 240 | CH$_3$ | H | CH$_3$ | D | H | OH | D |
| 241 | CD$_3$ | H | CH$_3$ | D | H | OH | D |
| 242 | CH$_3$ | H | CD$_3$ | D | H | OH | D |
| 243 | CD$_3$ | H | CD$_3$ | D | H | OH | D |
| 244 | CH$_3$ | H | CH$_3$ | D | D | OH | D |
| 245 | CD$_3$ | H | CH$_3$ | D | D | OH | D |
| 246 | CH$_3$ | H | CD$_3$ | D | D | OH | D |
| 247 | CD$_3$ | H | CD$_3$ | D | D | OH | D |
| 248 | CH$_3$ | CD$_3$ | CH$_3$ | H | H | taken together as =O | |
| 249 | CD$_3$ | CD$_3$ | CH$_3$ | H | H | taken together as =O | |
| 250 | CH$_3$ | CD$_3$ | CD$_3$ | H | H | taken together as =O | |
| 251 | CD$_3$ | CD$_3$ | CD$_3$ | H | H | taken together as =O | |
| 252 | CH$_3$ | CD$_3$ | CH$_3$ | H | D | taken together as =O | |
| 253 | CD$_3$ | CD$_3$ | CH$_3$ | H | D | taken together as =O | |
| 254 | CH$_3$ | CD$_3$ | CD$_3$ | H | D | taken together as =O | |
| 255 | CD$_3$ | CD$_3$ | CD$_3$ | H | D | taken together as =O | |
| 256 | CH$_3$ | CD$_3$ | CH$_3$ | D | H | taken together as =O | |
| 257 | CD$_3$ | CD$_3$ | CH$_3$ | D | H | taken together as =O | |
| 258 | CH$_3$ | CD$_3$ | CD$_3$ | D | H | taken together as =O | |
| 259 | CD$_3$ | CD$_3$ | CD$_3$ | D | H | taken together as =O | |
| 260 | CH$_3$ | CD$_3$ | CH$_3$ | D | D | taken together as =O | |
| 261 | CD$_3$ | CD$_3$ | CH$_3$ | D | D | taken together as =O | |
| 262 | CH$_3$ | CD$_3$ | CD$_3$ | D | D | taken together as =O | |
| 263 | CD$_3$ | CD$_3$ | CD$_3$ | D | D | taken together as =O | |
| 264 | CH$_3$ | CD$_3$ | CH$_3$ | H | H | OH | H |
| 265 | CD$_3$ | CD$_3$ | CH$_3$ | H | H | OH | H |
| 266 | CH$_3$ | CD$_3$ | CD$_3$ | H | H | OH | H |
| 267 | CD$_3$ | CD$_3$ | CD$_3$ | H | H | OH | H |
| 268 | CH$_3$ | CD$_3$ | CH$_3$ | H | D | OH | H |
| 269 | CD$_3$ | CD$_3$ | CH$_3$ | H | D | OH | H |
| 270 | CH$_3$ | CD$_3$ | CD$_3$ | H | D | OH | H |
| 271 | CD$_3$ | CD$_3$ | CD$_3$ | H | D | OH | H |
| 272 | CH$_3$ | CD$_3$ | CH$_3$ | D | H | OH | H |
| 273 | CD$_3$ | CD$_3$ | CH$_3$ | D | H | OH | H |
| 274 | CH$_3$ | CD$_3$ | CD$_3$ | D | H | OH | H |
| 275 | CD$_3$ | CD$_3$ | CD$_3$ | D | H | OH | H |
| 276 | CH$_3$ | CD$_3$ | CH$_3$ | D | D | OH | H |
| 277 | CD$_3$ | CD$_3$ | CH$_3$ | D | D | OH | H |
| 278 | CH$_3$ | CD$_3$ | CD$_3$ | D | D | OH | H |
| 279 | CD$_3$ | CD$_3$ | CD$_3$ | D | D | OH | H |
| 280 | CH$_3$ | CD$_3$ | CH$_3$ | H | H | OH | D |
| 281 | CD$_3$ | CD$_3$ | CH$_3$ | H | H | OH | D |
| 282 | CH$_3$ | CD$_3$ | CD$_3$ | H | H | OH | D |
| 283 | CD$_3$ | CD$_3$ | CD$_3$ | H | H | OH | D |
| 284 | CH$_3$ | CD$_3$ | CH$_3$ | H | D | OH | D |
| 285 | CD$_3$ | CD$_3$ | CH$_3$ | H | D | OH | D |
| 286 | CH$_3$ | CD$_3$ | CD$_3$ | H | D | OH | D |
| 287 | CD$_3$ | CD$_3$ | CD$_3$ | H | D | OH | D |
| 288 | CH$_3$ | CD$_3$ | CH$_3$ | D | H | OH | D |
| 289 | CD$_3$ | CD$_3$ | CH$_3$ | D | H | OH | D |
| 290 | CH$_3$ | CD$_3$ | CD$_3$ | D | H | OH | D |
| 291 | CD$_3$ | CD$_3$ | CD$_3$ | D | H | OH | D |
| 292 | CH$_3$ | CD$_3$ | CH$_3$ | D | D | OH | D |
| 293 | CD$_3$ | CD$_3$ | CH$_3$ | D | D | OH | D |
| 294 | CH$_3$ | CD$_3$ | CD$_3$ | D | D | OH | D |
| 295 | CD$_3$ | CD$_3$ | CD$_3$ | D | D | OH | D | or a pharmaceutically acceptable salt of the compound.

15. A pharmaceutical composition comprising a compound of claim 1 and a pharmaceutically acceptable carrier.

16. A method of treating a disease or condition in a patient in need thereof, comprising administering to the patient an effective amount of a composition of claim 15, wherein the disease is diabetic nephropathy, hypertensive nephropathy or intermittent claudication on the basis of chronic occlusive arterial disease of the limbs.

17. The compound of claim 1, wherein any atom designated as deuterium has an isotopic enrichment of at least 90%.

18. The compound of claim 17, wherein any atom designated as deuterium has an isotopic enrichment of at least 95%.

\* \* \* \* \*